United States Patent
Spahn

(10) Patent No.: US 10,448,914 B2
(45) Date of Patent: Oct. 22, 2019

(54) X-RAY IMAGE GENERATION

(71) Applicant: Martin Spahn, Erlangen (DE)

(72) Inventor: Martin Spahn, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 463 days.

(21) Appl. No.: 15/217,705

(22) Filed: Jul. 22, 2016

(65) Prior Publication Data
US 2017/0020475 A1   Jan. 26, 2017

(30) Foreign Application Priority Data
Jul. 23, 2015 (DE) .................. 10 2015 213 911

(51) Int. Cl.
*A61B 6/00* (2006.01)
*H04N 5/21* (2006.01)
(Continued)

(52) U.S. Cl.
CPC .............. *A61B 6/5205* (2013.01); *A61B 6/42* (2013.01); *A61B 6/4233* (2013.01);
(Continued)

(58) Field of Classification Search
CPC ....... A61B 6/42; A61B 6/4233; A61B 6/4241; A61B 6/4266; A61B 6/482; A61B 6/52;
(Continued)

(56) References Cited

U.S. PATENT DOCUMENTS 5,381,014 A   1/1995 Jeromin et al.
5,528,043 A * 6/1996 Spivey ................ A61B 6/4233
                                                  250/208.1
(Continued)

FOREIGN PATENT DOCUMENTS

DE   102004015876 A1   10/2005
DE   102012202500 A1    8/2013

OTHER PUBLICATIONS

Michael Hilton et al., "Wavelet Denoising of Functional MRI Data", Wavelets in Medicine and Biology, Chapter 4, pp. 93-114, CRC Press, Inc., 1996.
(Continued)

*Primary Examiner* — Allen C. Ho
(74) *Attorney, Agent, or Firm* — Lempia Summerfield Katz LLC

(57) ABSTRACT

Generation of an X-ray image of an object using a counting X-ray detector is provided. The X-ray detector includes detector modules that may be aligned adjacent to one another. Each of the detector modules is subdivided into a matrix having a plurality of pixels. The detector modules are arranged adjacent to one another on a common substrate. A sensor surface formed by the detector modules has a uniform matrix structure having a constant pixel pitch. At least one missing pixel is arranged within the sensor surface. Raw image data is acquired by a portion of the detector modules of the X-ray detector, the acquired raw image data is at least partially corrected, and further raw image data is calculated for the at least one missing pixel using the corrected raw image data. The X-ray image is calculated based on the corrected raw image data and the further raw image data.

20 Claims, 10 Drawing Sheets

(51) Int. Cl.
  *H04N 5/235* (2006.01)
  *H04N 5/335* (2011.01)
  *H04N 5/32* (2006.01)
(52) U.S. Cl.
  CPC .......... *A61B 6/4241* (2013.01); *A61B 6/4266* (2013.01); *A61B 6/482* (2013.01); *A61B 6/52* (2013.01); *A61B 6/5258* (2013.01); *A61B 6/58* (2013.01); *A61B 6/582* (2013.01); *A61B 6/585* (2013.01); *H04N 5/21* (2013.01); *H04N 5/235* (2013.01); *H04N 5/32* (2013.01); *H04N 5/335* (2013.01); *A61B 6/44* (2013.01); *A61B 6/4429* (2013.01); *A61B 6/4435* (2013.01); *A61B 6/4441* (2013.01); *A61B 6/4458* (2013.01); *A61B 6/5241* (2013.01)
(58) Field of Classification Search
  CPC ... A61B 6/5205; A61B 6/5241; A61B 6/5258; A61B 6/58; A61B 6/582; A61B 6/585
  USPC ....... 378/5, 19, 62, 98.8, 98.9, 98.11, 98.12, 378/207; 250/370.09
  See application file for complete search history.

(56) References Cited

U.S. PATENT DOCUMENTS

| | | | | |
|---|---|---|---|---|
| 5,584,292 | A * | 12/1996 | Cheung | A61B 6/4233 378/37 |
| 5,712,890 | A * | 1/1998 | Spivey | A61B 6/032 378/37 |
| 6,118,846 | A * | 9/2000 | Liu | G01N 23/04 378/62 |
| 6,296,387 | B1 * | 10/2001 | Guillemaud | H04N 5/32 348/E5.081 |
| 6,404,853 | B1 * | 6/2002 | Odogba | A61B 6/00 250/208.1 |
| 6,498,831 | B2 * | 12/2002 | Granfors | A61B 6/00 348/246 |
| 6,519,314 | B1 * | 2/2003 | Baba | A61B 6/00 250/370.09 |
| 6,529,618 | B1 | 3/2003 | Ohara et al. | |
| 6,529,622 | B1 * | 3/2003 | Pourjavid | H04N 5/367 250/370.09 |
| 6,594,339 | B1 * | 7/2003 | Alving | A61B 6/488 378/98.7 |
| 6,655,836 | B2 * | 12/2003 | Boehm | A61B 6/00 348/E5.081 |
| 6,663,281 | B2 * | 12/2003 | Aufrichtig | H04N 5/2178 348/E5.082 |
| 6,718,011 | B2 | 4/2004 | Spahn | |
| 6,763,084 | B2 | 7/2004 | Boehm et al. | |
| 6,919,568 | B2 * | 7/2005 | Odogba | A61B 6/585 250/336.1 |
| 7,013,036 | B2 * | 3/2006 | Inoue | H04N 5/374 250/208.6 |
| 7,057,179 | B2 * | 6/2006 | Arques | G01T 1/29 250/370.01 |
| 7,106,825 | B2 * | 9/2006 | Gregerson | G06T 11/005 378/19 |
| 7,136,454 | B2 * | 11/2006 | Gerndt | G01N 23/207 378/98.12 |
| 7,138,636 | B2 * | 11/2006 | Petrick | H04N 5/32 250/370.09 |
| 7,139,362 | B2 * | 11/2006 | Heismann | A61B 6/032 378/5 |
| 7,142,705 | B2 * | 11/2006 | Inoue | G06T 5/10 382/132 |
| 7,161,154 | B2 * | 1/2007 | Nascetti | H04N 3/1512 250/370.09 |
| 7,260,174 | B2 * | 8/2007 | Hoffman | A61B 6/032 250/363.09 |
| 7,263,167 | B2 * | 8/2007 | Walter | A61B 6/032 378/116 |
| 7,362,916 | B2 * | 4/2008 | Yamazaki | H04N 5/32 348/246 |
| 7,369,711 | B2 * | 5/2008 | Odogba | A61B 6/585 382/128 |
| 7,474,774 | B2 * | 1/2009 | Inoue | G06T 5/002 348/E5.086 |
| 7,634,061 | B1 * | 12/2009 | Tümer | G01T 1/247 378/62 |
| 7,639,849 | B2 * | 12/2009 | Kimpe | G09G 3/20 345/690 |
| 7,729,527 | B2 * | 6/2010 | Maschauer | G06T 5/50 378/98.7 |
| 7,819,581 | B2 * | 10/2010 | Srinivasan | G01T 7/005 378/19 |
| 7,822,173 | B2 * | 10/2010 | Mattson | A61B 6/585 378/19 |
| 7,863,575 | B2 * | 1/2011 | Enomoto | G01T 1/2018 250/363.07 |
| 7,864,993 | B2 * | 1/2011 | Maack | G06T 5/005 382/128 |
| 7,920,751 | B2 * | 4/2011 | Li | G01T 1/2985 250/200 |
| 7,943,907 | B2 * | 5/2011 | Eversmann | G01T 1/17 250/395 |
| 7,956,433 | B2 * | 6/2011 | Okada | H01L 27/14603 257/440 |
| 8,040,406 | B2 * | 10/2011 | Enomoto | H04N 1/401 348/246 |
| 8,064,715 | B2 | 11/2011 | Spahn | |
| 8,111,803 | B2 * | 2/2012 | Edic | A61B 6/4035 378/146 |
| 8,159,576 | B2 * | 4/2012 | Fujita | G01J 1/44 348/294 |
| 8,169,522 | B2 * | 5/2012 | Orava | G01T 1/2928 348/308 |
| 8,189,084 | B2 * | 5/2012 | Kyushima | H04N 5/32 348/294 |
| 8,198,596 | B2 * | 6/2012 | Kuwabara | G06T 5/005 250/370.08 |
| 8,218,047 | B2 * | 7/2012 | Kyushima | G06T 1/0007 348/302 |
| 8,294,793 | B2 * | 10/2012 | Kyushima | H04N 5/335 348/246 |
| 8,389,928 | B2 * | 3/2013 | Hackenschmied | G01T 1/249 250/252.1 |
| 8,440,957 | B2 * | 5/2013 | Dierickx | G01T 1/247 250/214 R |
| 8,450,695 | B2 * | 5/2013 | Kappler | G01T 1/17 250/370.09 |
| 8,483,359 | B2 * | 7/2013 | Fujita | H01L 27/14654 250/370.09 |
| 8,488,735 | B2 * | 7/2013 | Fujita | H01L 27/14656 378/19 |
| 8,513,614 | B2 * | 8/2013 | Kraft | G01T 1/1647 250/370.09 |
| 8,519,348 | B2 * | 8/2013 | Topfer | A61B 6/585 250/370.11 |
| 8,530,850 | B2 * | 9/2013 | Spartiotis | H01L 27/14634 250/370.08 |
| 8,547,464 | B2 * | 10/2013 | Kyushima | A61B 6/4233 348/246 |
| 8,610,803 | B2 * | 12/2013 | Omi | H04N 5/23293 348/246 |
| 8,625,741 | B2 * | 1/2014 | Kyushima | H04N 5/378 378/98.8 |
| 8,660,335 | B2 * | 2/2014 | Pavkovich | G06T 5/005 348/241 |
| 8,710,446 | B2 * | 4/2014 | Inoue | G01T 1/2928 250/252.1 |
| 8,829,455 | B2 * | 9/2014 | Nakatsugawa | A61B 6/4233 250/370.09 |
| 8,855,265 | B2 * | 10/2014 | Engel | A61B 6/00 378/36 |
| 8,894,280 | B2 * | 11/2014 | Topfer | A61B 6/585 250/252.1 |

(56) References Cited

U.S. PATENT DOCUMENTS

| | | | | |
|---|---|---|---|---|
| 8,937,626 B2* | 1/2015 | Omi | ............... | G06T 5/005 345/581 |
| 8,981,313 B2* | 3/2015 | Atzinger | ............... | G01T 1/2928 250/371 |
| 9,031,197 B2* | 5/2015 | Spahn | ............... | H04N 5/32 378/98.8 |
| 9,055,922 B2* | 6/2015 | Kuwabara | ............... | A61B 6/542 |
| 9,057,788 B2* | 6/2015 | Abraham | ............... | G01T 1/1647 |
| 9,060,738 B2* | 6/2015 | Kuwabara | ............... | A61B 6/548 |
| 9,063,240 B2* | 6/2015 | Herrmann | ............... | G01T 7/005 |
| 9,072,440 B2* | 7/2015 | Koishi | ............... | A61B 6/032 |
| 9,075,147 B2* | 7/2015 | Schröter | ............... | G01T 1/247 |
| 9,164,183 B2* | 10/2015 | Kraft | ............... | G01T 1/40 |
| 9,194,964 B2* | 11/2015 | Ito | ............... | H04N 5/32 |
| 9,195,899 B2* | 11/2015 | Topfer | ............... | G06K 9/38 |
| 9,207,332 B2* | 12/2015 | Spahn | ............... | G01T 1/2928 |
| 9,237,873 B2* | 1/2016 | Yin | ............... | A61B 6/032 |
| 9,289,184 B2* | 3/2016 | Lalena | ............... | H04N 17/002 |
| 9,348,036 B2* | 5/2016 | Yamakawa | ............... | G01T 1/24 |
| 9,351,701 B2* | 5/2016 | Yamakawa | ............... | A61B 6/025 |
| 9,354,184 B2* | 5/2016 | Dowaki | ............... | H04N 5/32 |
| 9,389,320 B2* | 7/2016 | Ogawa | ............... | A61B 6/14 |
| 9,417,339 B2* | 8/2016 | Spahn | ............... | G01T 1/247 |
| 9,417,345 B2* | 8/2016 | Reitz | ............... | G01T 7/005 |
| 9,513,175 B2* | 12/2016 | Prendergast | ............... | G01T 1/247 |
| 9,558,582 B2* | 1/2017 | Sakumura | ............... | G06T 15/08 |
| 9,599,730 B2* | 3/2017 | Spahn | ............... | G01T 1/247 |
| 9,602,745 B2* | 3/2017 | Nishihara | ............... | H04N 5/378 |
| 9,619,730 B2* | 4/2017 | Pavlovich | ............... | A61B 6/032 |
| 9,664,798 B2* | 5/2017 | Kappler | ............... | G01T 1/17 |
| 9,668,706 B2* | 6/2017 | Kim | ............... | A61B 6/547 |
| 9,678,220 B2* | 6/2017 | Herrmann | ............... | G01T 1/17 |
| 9,693,743 B2* | 7/2017 | Arakita | ............... | G01T 1/1606 |
| 9,700,268 B2* | 7/2017 | Kang | ............... | A61B 6/542 |
| 9,753,160 B2* | 9/2017 | Bellazzini | ............... | G01T 1/247 |
| 9,833,214 B2* | 12/2017 | Imamura | ............... | A61B 6/586 |
| 9,846,244 B2* | 12/2017 | Abraham | ............... | H04N 5/32 |
| 10,010,303 B2* | 7/2018 | Konno | ............... | A61B 6/032 |
| 10,048,391 B2* | 8/2018 | Steadman Booker | ............... | G01T 1/1648 |
| 10,078,009 B2* | 9/2018 | Daerr | ............... | G01J 1/44 |
| 10,105,114 B2* | 10/2018 | Shimizukawa | ............... | A61B 6/4283 |
| 2015/0218296 A1 | 8/2015 | Kaspar et al. | | |

OTHER PUBLICATIONS

Antoni Buades et al., "A Review of Image Denoising Algorithms, with a New One", SIAM Journal on Multiscale Modeling and Simulation: A SIAM Interdisciplinary Journal, vol. 4, No. 2, pp. 490-530, 2005 Soc. for Industrial and Applied Mathematics; 2005.
K. Bredies et al., "Mathematical Image Processing: Introduction to the principles and modern theory", Vieweg + Teubner Verlag; 2010.
Spahn Martin, "Flat detectors and their clinical applications", European Radiology, vol. 15, pp. 1934-1947, 2005.
German Office Action for related German Application No. 10 2015 213 911.5 dated Mar. 27, 2017, with English Translation.

* cited by examiner

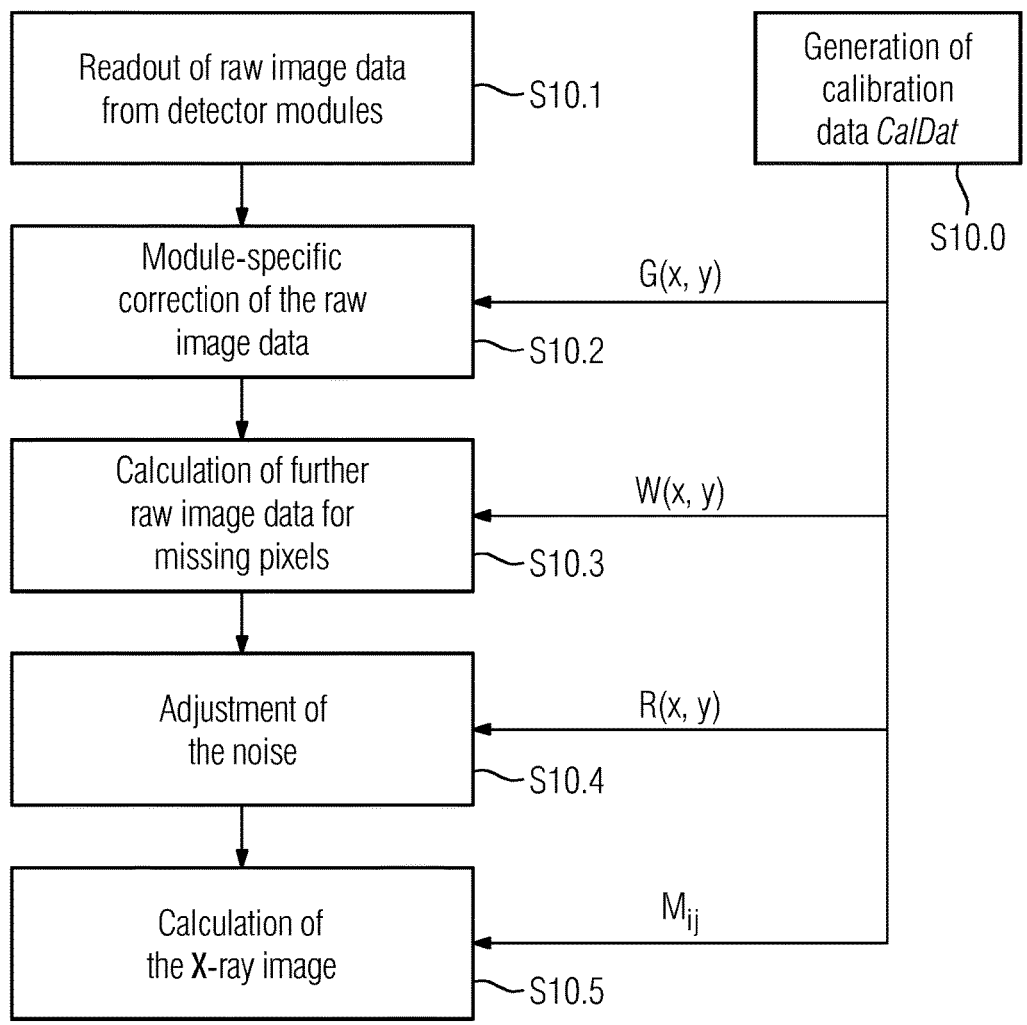
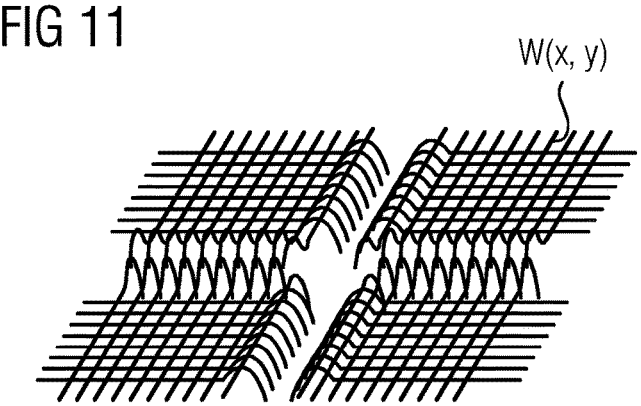

X-RAY IMAGE GENERATION

This application claims the benefit of DE 10 2015 213 911.5, filed on Jul. 23, 2015, which is hereby incorporated by reference in its entirety.

BACKGROUND

The present embodiments relate to generating an X-ray image of an object irradiated by X-ray radiation by an X-ray system including a counting digital X-ray detector.

X-ray systems are used for imaging for diagnostic examination purposes and for interventional procedures (e.g., in cardiology, radiology and surgery). Typically, X-ray systems have an X-ray tube and an X-ray detector, jointly mounted on a C-arm, for example, a high-voltage generator for generating the tube voltage, an imaging system, a system control unit, and a patient table. Biplane systems (e.g., C-arms) are likewise employed in interventional radiology. Generally, flat-panel X-ray detectors find application as X-ray detectors in many fields of medical X-ray diagnostics and intervention (e.g., in radiography, interventional radiology, cardioangiography, but also in therapeutic treatment applications for imaging within the context of monitoring and radiotherapy planning or mammography).

Flat-panel X-ray detectors in use today are generally integrating detectors and are based mainly on scintillators, composed of CsJ, for example, which convert X-ray radiation into comparatively low-energy radiation, visible light, for example. The light is converted into electrical charge in photodiode arrays. The photodiode arrays are then read out, typically row-by-row, via active control elements. FIG. 1 shows the basic structure of an indirectly converting flat-panel X-ray detector currently in use, having a scintillator 10, an active readout matrix 11 made of amorphous silicon or embodied in CMOS technology having a plurality of pixel elements 12 (e.g., with photodiode 13 and switching element 14) and drive and readout electronics 15 (see, for example, M. Spahn, "Flat detectors and their clinical applications", Eur Radiol. (2005), 15: 1934-1947).

The active readout matrix 11 typically consists of a plurality of tiles or shingles (not shown). In order to generate large surface areas of, for example, 22×22 cm², the matrix tiles are joined (e.g., 'butted') without gaps at the joints or else with a defined number of missing pixel rows or pixel columns. The function of the photodiodes 13 at the edge of such a tile is generally not constrained by their position. The scintillator 10 is generally embodied with a large surface area and covers a large number of tiles. This makes the overall behavior of the edge pixels in present-day integrating flat-panel detectors well-mannered such that either few or no corrections at all are to be made at the joints of the matrix tiles. Thus, in the event of defined pixel rows being missing between two matrix tiles, for example, trivial interpolation algorithms are employed in order to reconstruct the missing image information (e.g., the defect correction method described in the publication U.S. Pat. No. 6,763,084 B2) when, as described, defects occurring dynamically and not primarily at a fixed location are also handled.

Depending on beam quality, the quantum efficiency for a CsJ-based scintillator having a layer thickness of, for example, 600 µm ranges between approximately 50% and 80% (see, for example, M. Spahn, "Flat detectors and their clinical applications", Eur Radiol (2005), 15: 1934-1947). The spatial frequency dependent DQE(f) (Detective Quantum Efficiency) is upwardly limited as a result and lies significantly thereunder for typical pixel sizes of, for example, 150 to 200 µm and for the spatial frequencies of 1 to 2 lp/mm (e.g., line pairs per mm) that are of interest for the applications. In order to enable new applications (e.g., dual-energy, material separation, etc.), but also to increase the quantum efficiency further, use is increasingly being made of the potential of counting detectors or energy-discriminating counting detectors mainly based on direct-converting materials (e.g., such as CdTe or CdZTe=CZT) and contacted Application-Specific Integrated Circuits (ASICs) (e.g., implementation in CMOS technology). Other materials such as Si or GaAs may likewise be of interest for certain applications. Counting detectors count the incident X-ray quanta individually, instead of integrating the X-ray quanta as a whole, with the result that electronic noise may be suppressed almost completely.

An example layout of such counting X-ray detectors is illustrated in FIG. 2. X-ray radiation is converted in the direct converter 224 (e.g., CdTe or CZT), and the generated charge carrier pairs are separated via an electrical field that is generated by a common top electrode 26 and a pixel electrode 25. The charge generates a charge pulse in one of the pixel electrodes 25 of the ASIC 27 that are implemented as pixel-shaped. The height of the charge pulse corresponds to the energy of the X-ray quantum, and the charge pulse is registered as a count event if the charge pulse exceeds a defined threshold value. The threshold value serves to differentiate an actual event from electronic noise or, for example, also to suppress k-fluorescence photons in order to avoid multiple counts. The ASIC 27, a corresponding section of the direct converter 224, and a coupling between direct converter 224 and ASIC 27 (e.g., by bump bonds 36 in the case of direct-converting detectors) in each case form a detector module 35 having a plurality of pixel elements 12. The ASIC 27 is arranged on a substrate 37 and is connected to peripheral electronics 38. A detector module 35 may also have one or more ASICs 27 and one or more part-pieces of a direct converter 224, chosen according to requirements in each case.

Many of the direct converters 224 that promise high signals and count rates, such as CdTe or CZT, may only be fabricated at reasonable cost in small surface areas (e.g., 2×2 cm² or 3×3 cm²). ASICs 27 having a complex pixel structure, such as are required for counting detectors, may likewise only be produced with an acceptable yield in small surface areas. By greater investment of resources, somewhat larger surface areas such as, for example, 2×8 cm² or 3×6 cm² may be provided, such that, for example, four 2×2 cm² or two 3×3 cm²-sized direct converters 224 may be mounted onto the corresponding ASICs 27 in order to form a detector module 35 in combination. In any case, such detector modules 35 are nevertheless small compared to the overall size of an average flat-panel image detector, such as is required for applications in angiography (e.g., 20×20 cm² or 30×40 cm²). In order to obtain a sufficiently large counting X-ray detector, a plurality of detector modules 35 are aligned next to one another or in a matrix-like arrangement (e.g., on four sides in the case of rectangular/square-shaped detector modules).

The general schematic layout of a counting pixel element 12 is shown in FIG. 4. The electrical charge is collected in the pixel element 12 via the charge input 28 and amplified in the pixel element 12 with the aid of a charge amplifier 29 and a feedback capacitor 40. In addition, the pulse shape may be adjusted at the output in a pulse shaper (e.g., filter) (not shown). An event is counted by incrementing a digital memory unit 33 (e.g., adder or counter) by one when the output signal exceeds a selectable threshold value. This is detected via a discriminator 31. The threshold value may also be specified as a fixed analog value, but is generally applied via a digital-to-analog converter (DAC) 32 and is consequently variably adjustable over a certain range. The threshold value may be selectable either locally pixel-by-pixel, via the discriminator 31 (e.g., local discriminator) and the DAC 32 (e.g., local DAC), as shown, or globally for a plurality of/all pixel elements via a global discriminator and DAC, for example. Counts may subsequently be read out via a drive and readout unit or via peripheral electronics 38.

Over and above a global DAC, which serves, for example, for setting a specific keV threshold for an entire detector module or the entire X-ray detector, a further pixel-by-pixel matching may be provided in order to correct pixel-to-pixel fluctuations (e.g., fluctuations in amplifiers 29, local material inhomogeneities of the detector material, etc.). This pixel-by-pixel calibration or correction DAC generally has a much higher resolution than the global DAC and is settable, for example, over a keV range within which the pixel-to-pixel fluctuations are expected (e.g., 6 keV). If such a calibration or correction DAC is provided, then it is advantageous to perform the global DAC and the correction DAC separately on account of the cited different resolutions. The global DAC may then be configured with rather a lower resolution (e.g., 2 keV/bit), which generates a voltage that is present at each pixel element of the detector module or all detector modules of a detector and onto which a pixel-by-pixel correction voltage is superimposed pixel by pixel by way of a higher-resolution correction DAC (e.g., 0.1 keV/bit or 0.5 keV/bit). If a plurality of threshold values and counters are provided per pixel element (e.g., spectral imaging), then a plurality of global DACs are provided. A calibration or correction DAC may be provided for each discriminator if, for example, the circuit exhibits a non-linear response.

FIG. 5 shows a schematic for an entire array of counting pixel elements 12 (e.g., 100×100 pixel elements of 180 μm each). In this example, it would have a size of 1.8×1.8 cm$^2$. For large-area X-ray detectors (e.g., 20×30 cm$^2$), a plurality of detector modules 35 are combined with one another (e.g., approximately 11×17 modules would produce this surface area) and are connected via the common peripheral electronics. For the connection between ASIC 27 and peripheral electronics 38, use is made of Through Silicon Via (TSV) technology, for example, in order to provide the detector modules 35 are aligned next to one another in the tightest possible four-sided arrangement.

In the case of counting and energy-discriminating X-ray detectors, two or more different threshold values per pixel (e.g., four), as shown in FIG. 6, are introduced by four pairs made up of DAC 32 and discriminator 31, and the height of the charge pulse, corresponding to the predefined threshold values (e.g., discriminator threshold values), is classified into one or more of the digital memory units 33 (counters). The X-ray quanta counted in a specific energy range may then be obtained by calculation of the difference between the counter contents of two corresponding counters. The discriminators 31 may be set, for example, with the aid of digital-to-analog converters (DAC) 32, for the entire detector module or pixel by pixel within given limits or ranges. The counter contents of counting pixel elements 12 are read out module by module in succession via a corresponding readout unit.

Various effects may now lead to a situation where an absorbed X-ray quantum deposits energy not just in one pixel, but where a portion of the energy is deposited in the neighboring pixels due to processes such as charge sharing or fluorescence photons (e.g., k-fluorescence). This may lead to miscounts (e.g., to multiple counts or no count) if the respective deposited energies lie below the threshold values set at the pixels or also to incorrect assignment of the energy in the case of energy-discriminating detectors. In order to solve the above-described problem, summation and anticoincidence circuits in which the charge deposited in neighboring pixels within a given time interval (e.g., coincidence) is added together and assigned to a specific pixel and the summation signal is compared with the threshold value of a discriminator or a plurality of discriminators of the pixel may be used.

One of the critical points in the case of counting detectors is the modular structure. As already mentioned, the detector modules of a counting detector are significantly smaller than the detector modules of integrating detectors. In order to obtain a sufficiently large X-ray detector, a plurality of detector modules are aligned next to one another or in a matrix-like arrangement (e.g., on four sides in the case of rectangular/square-shaped detector modules).

For mechanical and thermal reasons (e.g., precision with which the modules may be produced, dimensions, etc.), a gap, for example, in the form of rows or columns of pixels (e.g., in the x- and/or y-direction) that are insensitive to X-ray radiation, generally arises unintentionally between adjacently arranged modules. This may lead, for example, to one or more rows of missing pixels in each case between the modules. In a design that manages without missing pixels, the edge pixels of detector modules exhibit a different signal response due to the design compared to pixels arranged centrally on a detector module. This is attributable, for example, to the deformation of the electrical field at the edge of the X-ray converter due to the missing neighboring pixels on at least one side (known as discontinuity). For example, a lower efficiency of the charge collection in the edge pixels may lead to lower pulse heights, and this may lead to a changed count rate behavior above the defined energy thresholds. Given otherwise comparable conditions (e.g., with homogeneous X-ray flux and the same location-independent X-ray spectrum), the noise performance at the edge of a detector module may be changed by comparison with more centrally arranged pixels. In the case of ASICs that support energy summation and anticoincidence circuits of neighboring pixels, there is the problem that this generally may not be realized beyond ASIC boundaries. In other words, pixels arranged at peripheral positions on a detector module may also behave differently from centrally arranged pixels in terms of energy deposition and energy restoration. Further, fluorescence photons may escape more easily at the edges of the direct converter because no reabsorption may take place there due to the absence of material. Depending on X-ray beam quality and/or object to be examined, scatter radiation effects may manifest themselves differently at the module edges than in the center of the module. Also, given a comparable incident X-ray flux, an effectively smaller active surface of edge pixels of a detector module by design may generally lead to a smaller count rate and lower signal-to-noise ratio. The active surface area of edge pixels may be reduced in size due to a guard ring, for example. A guard ring in the form of an electrode defines the properties at the detector module edges and in certain cases improves the properties of peripherally arranged pixels.

A further problem may arise because electrical contacts are to be brought out vertically rather than laterally through the silicon of the ASIC chip with the aid of TSV technology, thereby providing the electrical connection (e.g., voltage supply of the chips, control and data lines) to the underlying electronics. Such TSVs use vertical openings that, depending on silicon thickness, are, for example, 100 µm to 200 µm in size and accordingly may assume pixel size. Surface area within the detector is likewise not available for the signal generation.

The quality of the resulting X-ray images suffers markedly due to the increased number of discontinuities occurring as a result of the small-scale granularity of the modular structure of counting detectors.

SUMMARY AND DESCRIPTION

The scope of the present invention is defined solely by the appended claims and is not affected to any degree by the statements within this summary.

The present embodiments may obviate one or more of the drawbacks or limitations in the related art. For example, the acquisition of an X-ray image by a counting X-ray detector that has been produced from the cited materials and has an improved quality and overcomes the described disadvantages is provided.

This may be achieved by a method for generating an X-ray image by an X-ray system including a counting X-ray detector as well as a data processing device for implementing the method.

Features, advantages or alternative variants mentioned in this context may be applied also to the other claimed subject matters, and vice versa. In other words, physical devices, for example, may also be developed using features described in connection with a method. In this case, the corresponding functional features of the method are embodied by corresponding physical modules or units One or more of the present embodiments relate to a method for generating an X-ray image of an object using an X-ray system including a counting X-ray detector. The X-ray detector may be a digital X-ray detector. The X-ray detector includes a plurality of detector modules that may be aligned adjacent to one another, where each detector module has an X-ray converter and is subdivided into a matrix having a plurality of pixels. The detector modules are arranged adjacent to one another on a common substrate. The sensor surface formed by the totality of the detector modules has a uniform matrix structure having a constant pixel pitch. At least one missing pixel is arranged within the sensor surface. For example, missing pixels may be arranged between neighboring detector modules and/or at the outer edge of detector modules arranged peripherally in the sensor surface. A detector module may have any desired shape permitting a regular serial concatenation in order to form a uniform, two-dimensional matrix structure within the sensor surface. For example, a detector module may have a hexagonal, a rectangular, or a square basic shape. In order to form the sensor surface, further detector modules may be arranged in series only in one or more spatial directions. In this way, X-ray detectors including only one row of adjacently arranged detector modules may be embodied, or planar X-ray detectors may be embodied.

The method includes acquiring raw image data using a plurality of detector modules of an X-ray detector. The acquired raw image data is at least partially corrected. Further raw image data is corrected for the at least one missing pixel using the corrected raw image data. The X-ray image is calculated based on the corrected raw image data and the further raw image data.

One or more of the present embodiments are based on the consideration that image information that is not present locally due to missing pixels may be reinstated subsequently from acquired, gap-affected raw image data by, in the first instance, correcting the acquired raw image data having design-related errors around the errors and using the corrected raw image data as a basis for calculating the further raw image data for the positions of the missing pixels. By using the further raw image data and the corrected raw image data, an X-ray image that possesses good image quality may thus be calculated. The correction of the acquired raw image data is incorporated twice into the X-ray image, once directly through the use of the corrected raw image data for the generation of the X-ray image and once indirectly through inclusion of the corrected raw image data in the calculation of the further raw image data.

In one embodiment, the X-ray detector is an X-ray detector including X-ray converters embodied as direct converters (e.g., made of CZT or CdTe). A pixel pitch is to be understood as the distance between the center points of directly neighboring pixels. Missing pixels are pixels that are not present or virtual pixels. These are arranged, for example, in gaps between detector modules or at the edge of the sensor surface of the X-ray detector and are usually design-related. For example, one row in each case or a plurality of adjacent rows and/or columns of virtual missing pixels may extend between detector modules. For example, the width of the gap between two neighboring detector modules corresponds to a multiple of the pixel pitch. A missing pixel may also be a real pixel (e.g., one that is present, but defective) that, for example, delivers a degraded signal response or no signal response due to defective circuits in the ASIC, vacancies in the X-ray converter, or faulty contacting of converter material and pixels of the ASIC or suchlike Real missing pixels occur primarily at arbitrary positions within the sensor surface. To sum up, in the region of a missing pixel, the X-ray detector is insensitive or sensitive only to a limited extent to incident X-ray radiation. The at least partial correction of the acquired raw image data includes correcting the signal contents of selected real (e.g., present and intact) pixels within the sensor surface. Alternatively, the signal contents of all real and intact pixels within the sensor surface may be corrected. No missing pixels are taken into account in the correction act, however. In the next act, further raw image data (e.g., additional, new image information) is calculated for at least one missing pixel (e.g., all missing pixels), which information may replace already existing image information at least in the case of a defective pixel. The corrected raw image data may be used in its entirety or in parts for this act. Alternatively or in addition, the calculation of the further image information may also be based on raw image data not taken into account by the correction act.

By correcting the acquired raw image data, a considerable improvement may be achieved with regard to further raw image data that is to be calculated based on the correction. In other words, more realistic further raw image data may be generated based on the corrected acquired raw image data. According to one or more of the present embodiments, through the use of corrected and further raw image data for calculating the X-ray image, an X-ray image is calculated which overall conveys an excellent image impression expected by a viewer.

According to a variant, the at least partial correction of the acquired raw image data includes adjusting the signal contents of a plurality of pixels (e.g., pixels arranged in the edge zones of a detector module) with regard to a uniform signal response at least within the detector module. The edge pixels of detector modules are adversely affected by a reduced signal quality due to position. This includes a degraded signal response as well as a poorer signal-to-noise ratio.

Signal response may be understood as the transfer function between incident X-ray quanta and detected or counted events. Edge pixels are intended to include not only pixels that are arranged directly at peripheral positions on the detector module, but may also include pixel rows lying further inward (e.g., the second, third and fourth pixel row, viewed from the edge of a detector module). Aligning the signal response for all pixels (e.g., all real pixels within a detector module) leads to an improvement in image quality of the X-ray image. For this purpose, only real pixels of the outer pixel rows may be corrected. Alternatively, all real pixels of a detector module are adjusted with regard to a uniform signal response, since pixels arranged close to the center in the detector module may also exhibit a differing signal response. Adjusting the pixels with regard to a uniform signal response may be adjusting the respective signal contents of the pixels.

According to an alternative, the response behavior of pixels may also be aligned across a plurality or all of the detector modules. In order to enable an alignment of the signal contents to a uniform response behavior to be made, the signal responses of all pixels are determined beforehand as part of a calibration in that the detector is irradiated by X-ray radiation of a known spectrum, for example, directly or using a phantom of defined attenuation properties, from which correction data for the individual pixels may be derived.

According to a further embodiment, the at least partial correction of the acquired raw image data is carried out taking into account the spectrum of the X-ray radiation applied in order to acquire the raw image data. This approach is based on the knowledge that the signal responses of pixels of the X-ray detector are dependent on the spectrum of the incident X-ray radiation. Accordingly, correction data for different X-ray spectra may be determined during a calibration act and be stored ready for retrieval. Alternatively or in addition, correction data for spectra that have not been measured may be obtained by interpolation of existing correction data associated with other spectra. For example, in the case of counting energy-discriminating detectors, correction data may be determined individually for each threshold value present at a pixel for different spectra of the incident X-ray radiation in the course of the calibration act and be stored ready for retrieval. The calibration act may be performed at any desired time prior to the acquisition of the raw image data.

According to a development, the at least partial correction of the acquired raw image data includes a multiplication of the signal contents of the plurality of pixels by a previously determined correction factor. In other words, the at least partial correction entails a linear adjustment of the signal responses. In the simplest case, the correction corresponds to a linear gain correction. Alternatively, non-linear corrections (e.g., a non-linear gain correction) or other methods, such as described, for example, in the patent specification U.S. Pat. No. 8,064,715 B2, find application.

In a further embodiment, the correction of the raw image data has an advantageous effect, whereby the at least partial correction of the acquired raw image data includes noise suppression with respect to the signal contents of the plurality of pixels. As mentioned in the introduction, the signal-to-noise ratio of a pixel also deteriorates (e.g., is reduced) with a degraded signal response. In other words, the noise component in the signal content becomes greater. Accordingly, the noise signal is simultaneously increased as a result of the adjustment of the signal response by, for example, a percentage increase in the signal content by multiplication with a correction factor. Noise reduction may be beneficial in order to counteract this effect. A known noise reduction method is described, for example, in *Mathematische Bildverarbeitung: Einführung in Grundlagen und moderne Theorie* (('*Mathematical image processing: Introduction to basics and contemporary theory*') K. Bredies, D. Lorenz; published by Vieweg+Teubner Verlag).

In a development, the calculation of the further raw image data includes interpolating and/or extrapolating the corrected raw image data onto the at least one missing pixel. In other words, further raw image data is generated for missing pixels based on the corrected raw image data. In this case, an interpolation may be employed when a missing pixel is arranged between two detector modules or within the surface area of one detector module. In this case, all real, non-defective pixels from the environment of the missing pixel may be taken into account together with their corrected or original signal contents. An extrapolation comes into consideration for missing pixels that are located at the edge of a detector module lying at a peripheral position within the sensor surface of the X-ray detector. Here, image information of the real pixels surrounding a missing pixel is present on one side only. In this case, not only the direct neighbors of the missing pixel are considered. Rather, pixels located at any distance away may be included in the interpolation/extrapolation (e.g., the immediate and next-nearest neighbors and the neighbors lying in the following two rows being taken into account).

According to an embodiment, the interpolation and/or extrapolation include/includes a weighted summation of the signal contents of pixels surrounding the at least one missing pixel. In this case, real and intact pixels may be taken into account.

According to a further embodiment, the signal contents of the surrounding pixels are weighted as a function of the distance between individual pixel and missing pixel. In one embodiment, the weighting factors for individual pixels are yielded from the inverse of the distance from the missing pixel. This approach is preceded by the consideration that the interpolation or extrapolation nodes are arranged as close as possible to a missing pixel in order to enable the local contrast to be reconstructed while approximately maintaining the spatial resolution. It therefore follows that the signal contents of pixels arranged closer to the missing pixel should figure more heavily in the weighting than the pixels located further away.

In spite of the above-described correction measures, however, the signal quality of peripheral pixels of a detector module, for example, is comparatively poorer than pixels arranged more centrally in the detector module, since at least on one side the pixels have no pixel neighbors. The image information at the interpolation or extrapolation nodes may be as reliable as possible in order to obtain a good end result.

From this, there follows a further embodiment, whereby pixels arranged peripherally on a detector module are incorporated with the weakest weighting if the at least one missing pixel is arranged between two detector modules and has peripheral pixels and/or further missing pixels as direct neighbors or is arranged close to the edge of the detector module and has peripheral pixels as direct neighbors. In this way, the error-affected signal content of the peripheral pixels may be suppressed in the interpolation and/or extrapolation. Peripheral pixels are the pixels of a detector module that are arranged directly at the edge of a detector module. The peripheral pixels form the outermost real pixels of a detector module.

There also follows from this the further embodiment, whereby pixels that are spaced at a distance from the at least one missing pixel corresponding to the double, triple or quadruple of the pixel pitch are incorporated with the heaviest weighting if the at least one missing pixel is arranged between two detector modules and has peripheral pixels and/or further missing pixels as direct neighbors. Both approaches produce individually or in combination a compromise between maintaining a good or adequate spatial resolution and an adequate signal quality at the missing pixel. In other words, this causes the interpolation or extrapolation nodes to be arranged somewhat further away from a missing pixel. The error-affected image information of peripheral pixels may be suppressed in this way, and a comparable spatial resolution may be maintained.

In a development, the calculation of the further raw image data for the at least one missing pixel includes a noise enhancement. The noise from the variance of neighboring pixels having good signal quality may be measured locally, for example, and the noise value or a fraction of the value (e.g., positive or negative) determined by random variable may be added to the noise distribution (e.g., Gaussian). The noise enhancement may be embodied in an arbitrarily complex manner in that it is determined, for example, whether the environment of a pixel under consideration is flat, in which case the variance would be given by the noise, or whether a gradient, and consequently structure, is present in one of the neighbor pixels. In this case, the variance would overvalue the noise due to the fact that the variance takes local signal changes into account. In this case, such neighbor pixels would be excluded when determining the variance. This measure enables an improved, homogeneous noise impression to be created in the X-ray image across detector module boundaries.

According to a further embodiment, the discriminator threshold value corresponding to a desired X-ray quantum energy to be detected is adjusted in a pixel-specific manner prior to the acquisition of the raw image data. As mentioned in the introduction, individual pixels of the cluster may be subject to pixel-specific fluctuations, due, for example, to vacancies in the converter material, with regard to the threshold value to be measured. Using the described approach, it is provided that all pixels actually capture signal contents with respect to the same X-ray spectrum. Reference may be made to previously generated calibration data for this purpose. The threshold value may be a unilateral threshold value or a bilateral threshold value, known as an energy bin. The pixel-specific adjustment may similarly be carried out with regard to counting energy-discriminating detectors for different threshold values that are settable or present at a pixel.

One or more of the present embodiments further relate to a data processing device of a counting X-ray detector and/or an X-ray system including the X-ray detector. The X-ray detector includes a plurality of detector modules that may be aligned adjacent to one another. Each detector module of the plurality of detector modules has an X-ray converter and is subdivided into a matrix having a plurality of pixels. The plurality of detector modules are arranged adjacent to one another on a common substrate. The sensor surface formed by the totality of detector modules has a uniform matrix structure having a constant pixel pitch. At least one missing pixel is arranged within the sensor surface (e.g., between neighboring detector modules and/or at the outer edge of detector modules arranged peripherally in the sensor surface). The data processing device is configured to perform the method of one or more of the present embodiments. The data processing device includes an interface unit configured to acquire raw image data from a plurality of detector modules of the X-ray detector. The data processing device also includes a correction unit configured for at least partially correcting the acquired raw image data, a first calculation unit that is configured to calculate further raw image data for the at least one missing pixel using the corrected raw image data, and a further calculation unit configured to calculate the X-ray image based on the corrected data and the further raw image data.

The term data processing device may be a computer or a plurality of computers engaged in data exchange with one another, each including at least one processor. The data processing device may be embodied as part of an X-ray detector or as part of an X-ray system. As part of the X-ray detector, the data processing device may be part of the peripherals. As part of the X-ray system, the data processing device may be embodied as part of the control unit or of the computing unit or may be assignable in parts to both. The individual units of the data processing device may be embodied as separate units or form one physical unit.

According to a development, the correction unit of the data processing device is configured to adjust the signal contents of a plurality of pixels (e.g., pixels arranged in the edge zones of a detector module) with regard to a uniform signal response at least within the detector module.

According to a further embodiment, the first calculation unit of the data processing device is configured to calculate further raw image data for the at least one missing pixel using an interpolation and/or extrapolation of the corrected raw image data onto the at least one missing pixel.

In a development, the data processing device also includes a noise correction unit configured to apply noise reduction or noise enhancement algorithms to the corrected and/or further raw image data.

With regard to a detailed description and/or advantages of individual aspects of the data processing device according to one or more of the present embodiments, reference is made to the explanations relating to the method, which may be applied analogously to the device.

In a further embodiment, the X-ray system may be embodied, for example, as a computed tomography system, angiography system, mobile or robot-controlled C-arm system, projection radiography system, or the like.

BRIEF DESCRIPTION OF THE DRAWINGS

The above-described characteristics, features, and advantages of the present invention, as well as the manner in which these are achieved, will become clearer and more readily understandable in connection with the following description of the exemplary embodiments, which are explained in more detail in conjunction with the drawings. No limitation of the invention to the exemplary embodiments is implied by this description. In the figures:

FIG. 10 is a flowchart of the method in another exemplary embodiment;

FIG. 11 shows a weighting function W(x,y) according to an exemplary embodiment;

DETAILED DESCRIPTION

Figure 1:
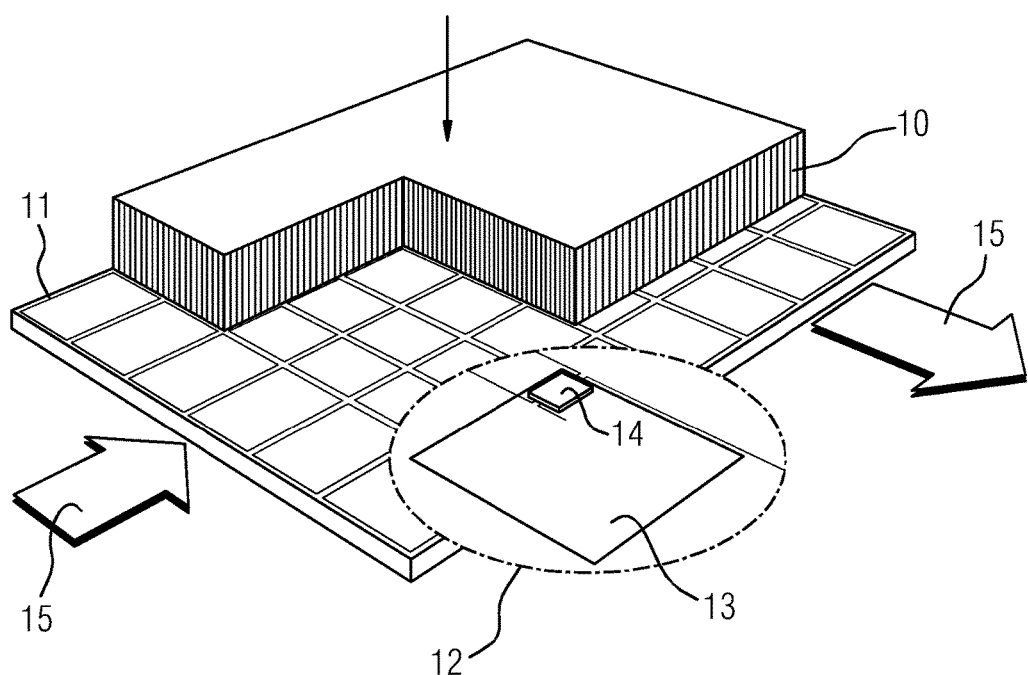
FIG. 1 shows a view of a known X-ray detector having a scintillator.
Figure 2:
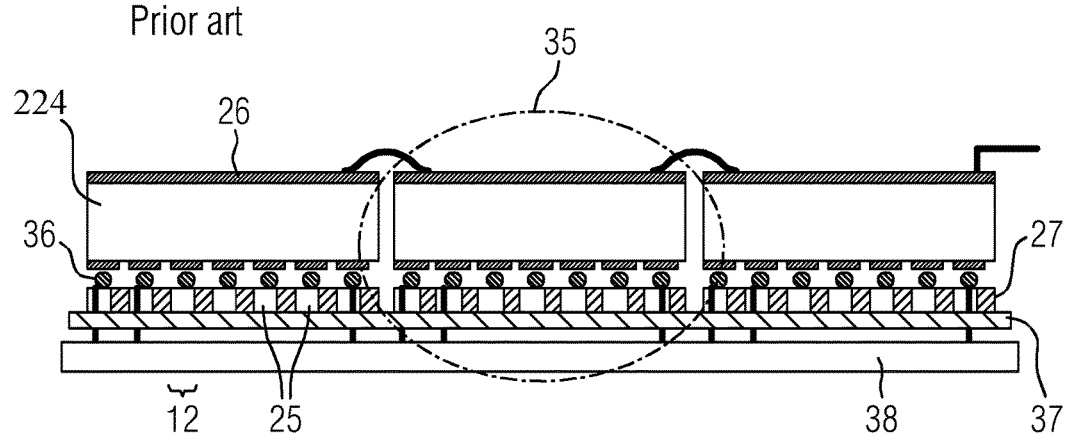
FIG. 2 shows a cross-section through a section of a known X-ray detector having a plurality of detector modules.
Figure 3:
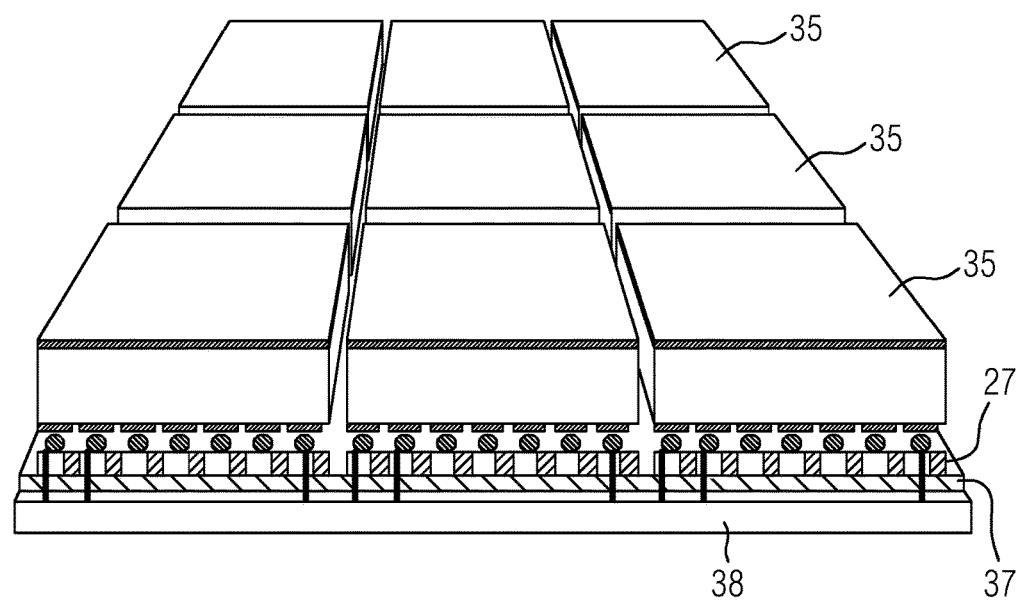
FIG. 3 shows a perspective plan view onto a section of a known X-ray detector having a plurality of detector modules.
Figure 4:
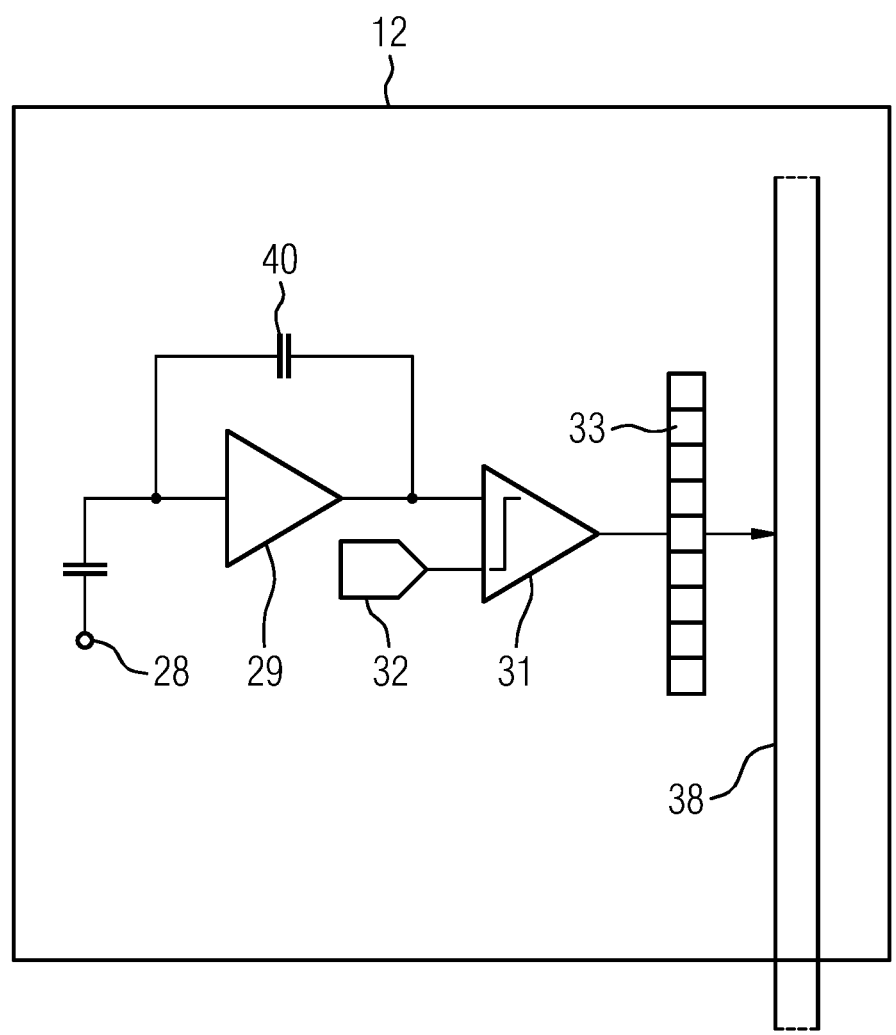
FIG. 4 is a schematic representation of the central functional elements of a counting pixel element of a known X-ray detector.
Figure 5:
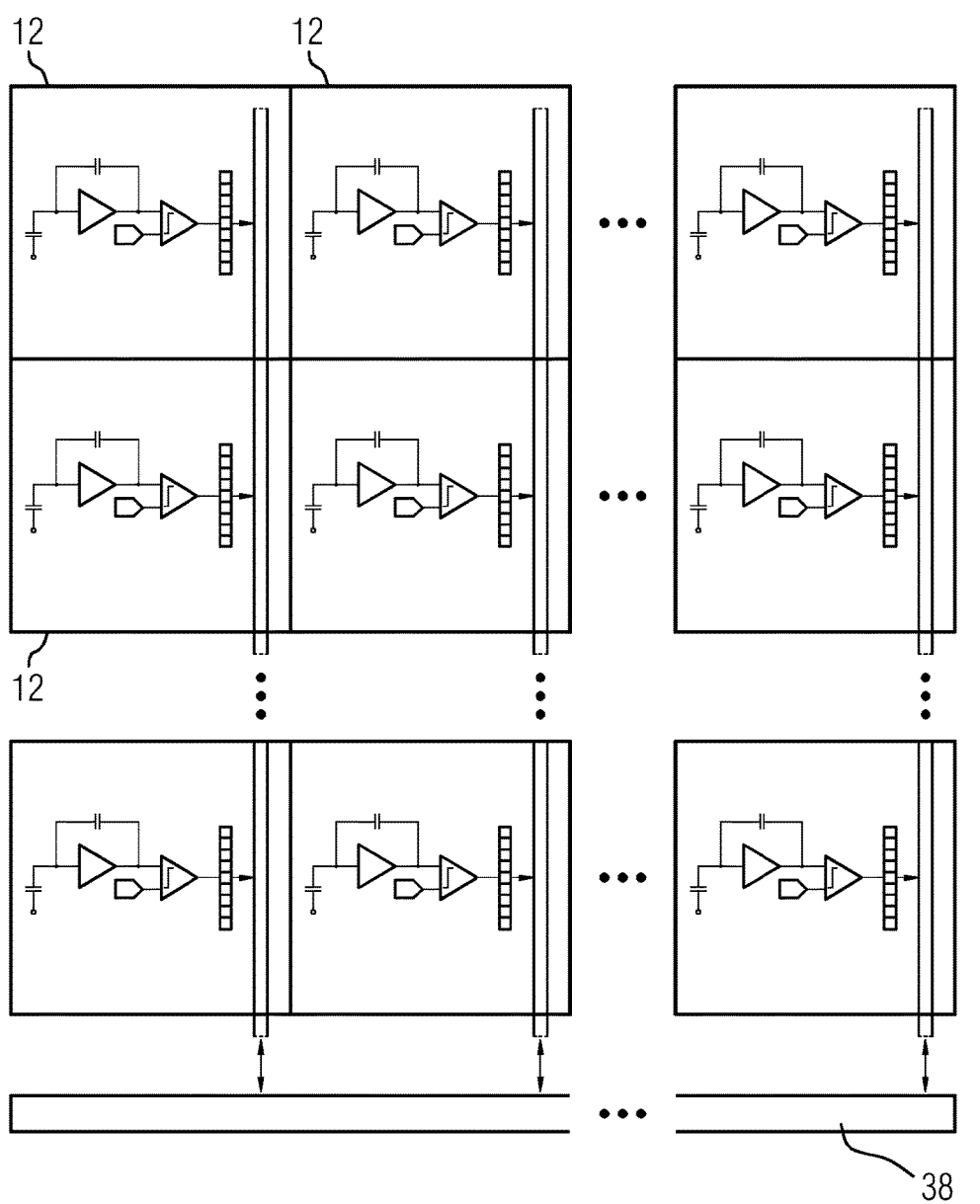
FIG. 5 is a schematic representation of a matrix composed of counting pixel elements of a known X-ray detector having drive and readout logic.
Figure 6:
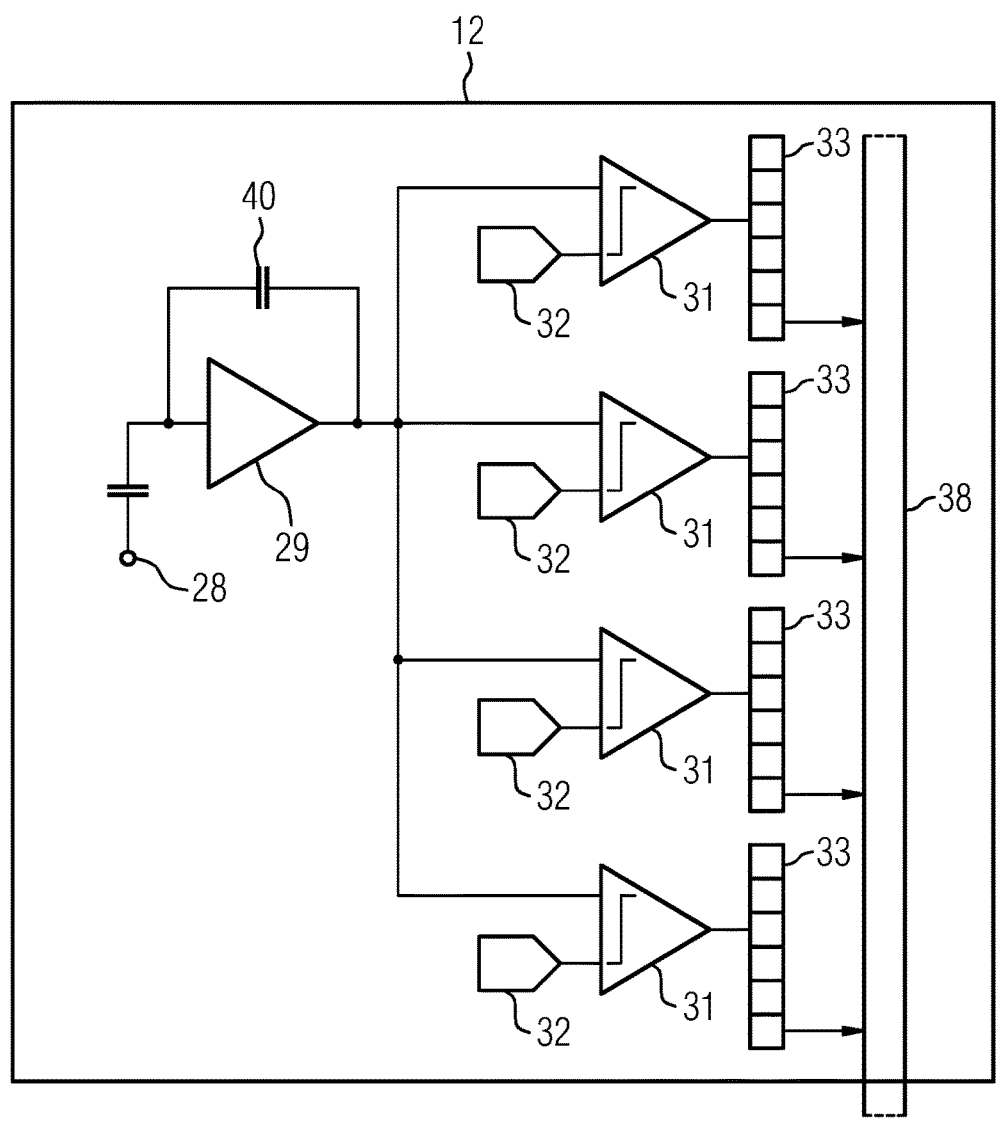
FIG. 6 is a schematic representation of the central functional elements of a pixel element of a known counting energy-discriminating X-ray detector.
Figure 7:
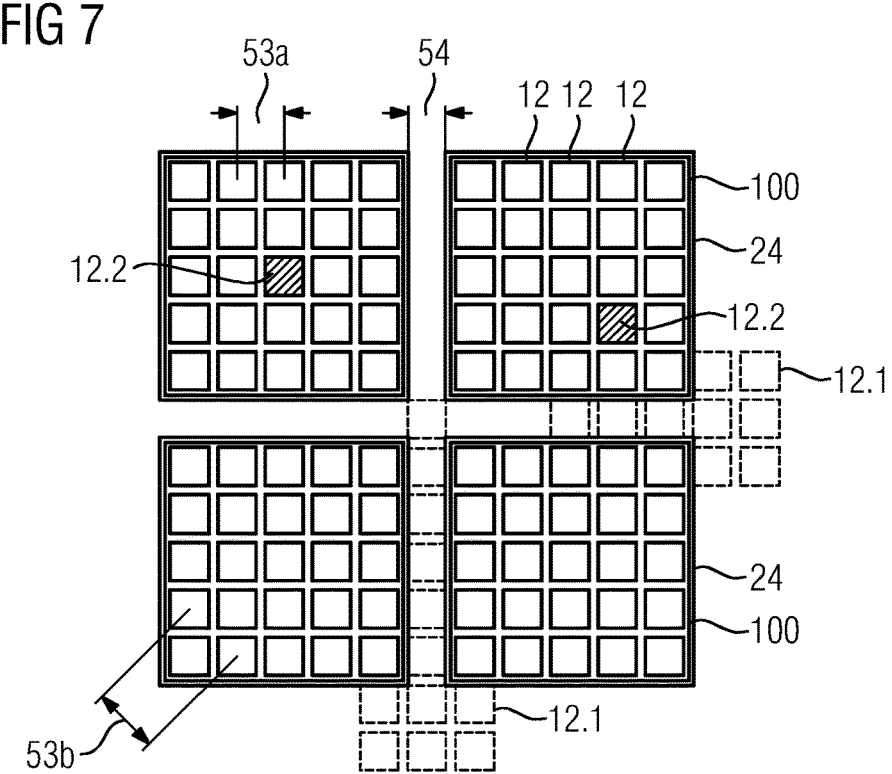
FIG. 7 is a schematic representation of four neighboring detector modules of an X-ray detector.
Figure 12:
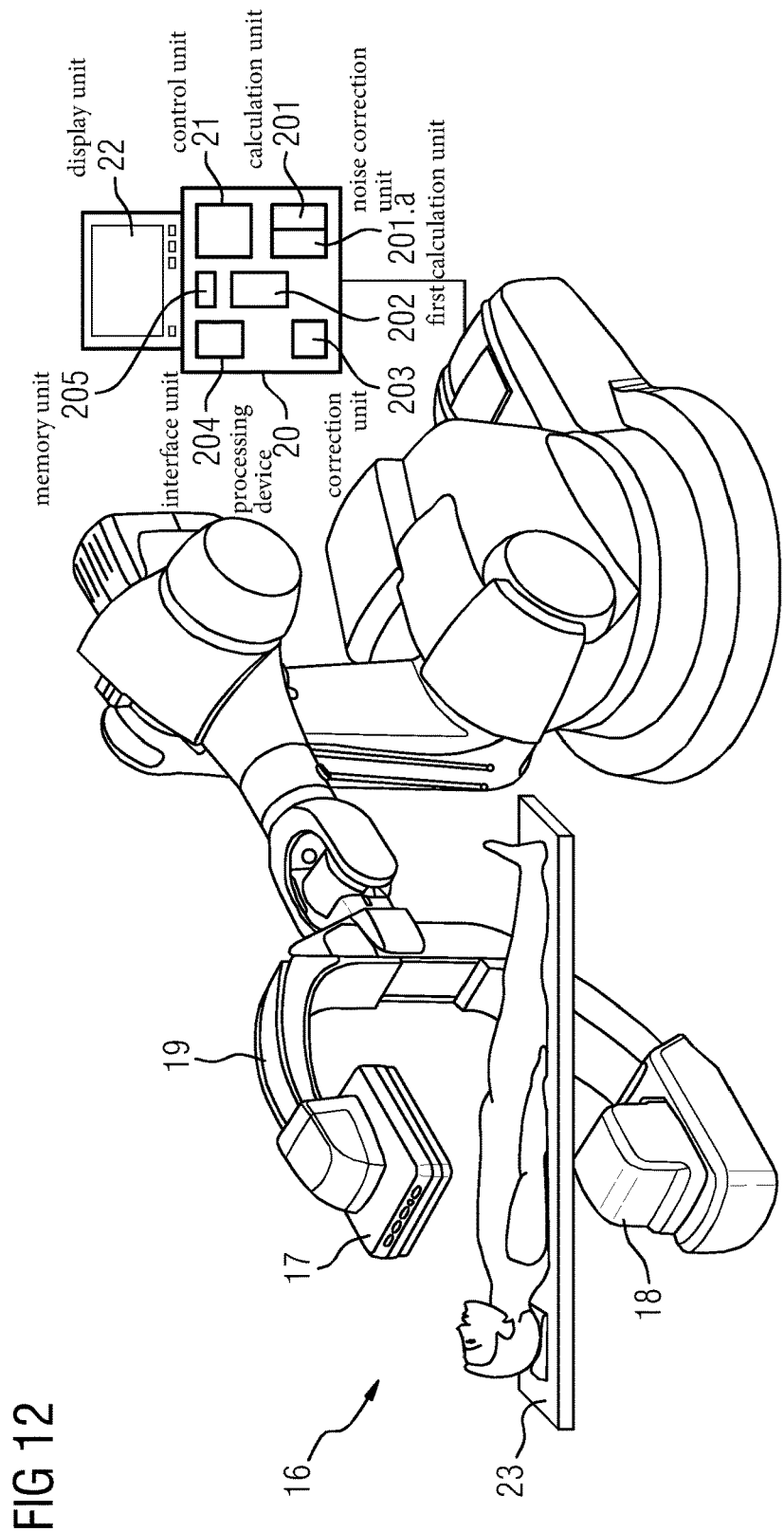
FIG. 12 shows an X-ray system including a data processing device according to an exemplary embodiment.

FIG. 7 shows a plan view onto four exemplary neighboring detector modules 24 of a counting digital X-ray detector 17 shown in FIG. 12, as may find application in combination with one or more of the present embodiments. The detector modules 24 shown are suitable for alignment next to one another on four sides, which provides that the counting digital X-ray detector 17 may have an arbitrary number of such detector modules 24 adjacent to one another. However, the detector modules 24 may also be rectangular or have some other shape that provides a regular matrix structure (e.g., hexagonal in the case of hexagonal pixels). In the present case, for greater clarity of illustration, each detector module 24 has only 5×5 pixels 12. A far greater number of pixels per detector module 24 may be provided. Each detector module 24 is subdivided into a plurality of equal-sized, square-shaped pixels 12 that are arranged in a matrix-like structure and have a regular pixel pitch 53*a* as well as a regular pixel diagonal pitch 53*b*. Each detector module 24 includes a protective ring electrode 100, also known as a guard ring, which is configured, for example, to prevent or minimize field inhomogeneities due to missing pixel neighbors at the module edges. The detector modules 24 are arranged such that the regular matrix structure has no interruption. A gap 54 is arranged between the detector modules 24. As shown by the virtual pixels 12.1 indicated by a dashed outline, the gap 54 is embodied so that one pixel 12.1 or one row or column of pixels 12.1 is missing. However, in other embodiments, two or three pixel rows may be missing. The gap 54 corresponds to a vacancy (e.g., missing pixels). Within the vacancy, the counting digital X-ray detector 17 is not sensitive to incident X-ray radiation. X-ray radiation incident within the vacancy is lost for the purposes of image generation. Two of the detector modules 24 shown include, by way of example, further missing pixels in the form of real, defective pixels 12.2 that are characterized by a degraded or non-existent signal response. X-ray radiation incident on the counting digital X-ray detector 17 at these points is also lost for the image generation or is unsuitable due to containing errors. Image information missing in the regions of the missing, virtual, and/or defective pixels 12.1, 12.2 may be reconstructed or obtained by the method according to one or more of the present embodiments, as will be described hereinbelow.

Figure 8:
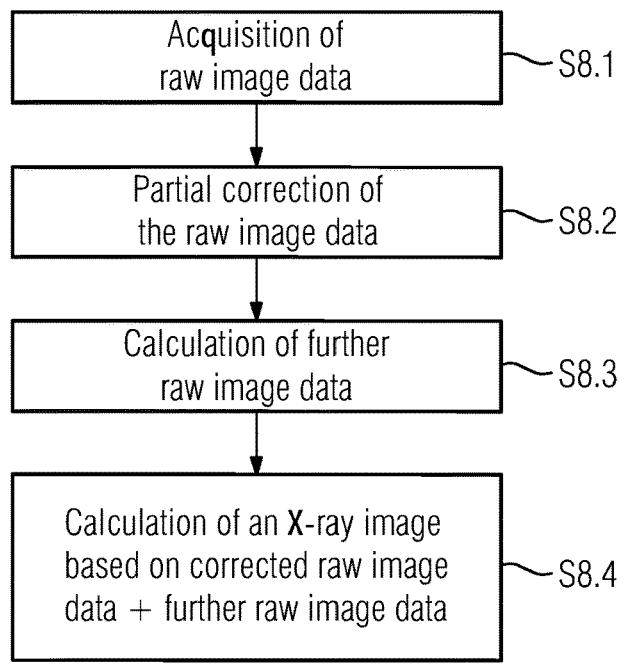
FIG. 8 is a flowchart of one embodiment of a method.

FIG. 8 shows a flowchart of a method in an exemplary embodiment. In act S8.1, raw image data is acquired by an X-ray system 16. The acquisition includes the image data acquisition. An examination subject is irradiated with X-ray radiation, and the attenuated X-ray radiation is detected, for example, by an X-ray detector 17 embodied according to FIG. 12. The acquisition also includes the readout of the detector modules 24 as well as the transfer of the raw image data to a data processing device 20 that, according to one or more of the present embodiments, is configured to reconstruct missing image information. In act S8.2, the acquired raw image data is corrected at least in parts. This provides that either all of the acquired raw image data is subjected to the correction step or only the raw image data acquired by selected pixels 12 or selected detector modules 24 is subjected to the correction step. For example, the raw image data of edge pixels 12 of detector modules 24 is corrected. Within the scope of the correction, the raw image data is adjusted, for example, with regard to a uniform signal response of the pixels 12 under consideration. The image information of the raw image data is improved as a result of the correction, such that a calculation of further raw image data based thereon will deliver good (e.g., realistic) results. The correction may be carried out, for example, based on correction data that has been generated by calibration of the X-ray detector 17 and is stored in retrievable form in a memory 205. In act S8.3, further raw image data is calculated from the corrected raw image data for missing pixels 12.1, 12.2 within the sensor surface of the X-ray detector 17. Missing pixels include both virtual (e.g., non-existent) pixels 12.1 and defective pixels 12.2 having an error-affected signal response. Whereas virtual pixels 12.1 may be arranged between detector modules 24 or at the outer edges of detector modules 24 arranged peripherally on the sensor surface of the X-ray detector 17, defective pixels 12.2 may occupy any position. The calculation includes an interpolation and/or an extrapolation of the corrected raw image data from the environment of missing pixels onto the missing pixels. In this case, the environment includes two, three, or more pixel rows surrounding a missing pixel. In order to obtain a good spatial resolution in the missing pixels also, a distance-dependent weighting of the neighboring pixels 12 is carried out during the interpolation and/or extrapolation. The further away a pixel 12 taken into account for the calculation is, the lower the contribution of the pixel 12 is. It is also taken into account that, in spite of the correction step, peripheral pixels 12 of a detector module 24 have a comparatively poor signal quality in relation to pixels 12 arranged centrally on the detector module 24. If a missing defective pixel 12.2 is located, for example, centrally within a detector module 24, a constant signal quality may be assumed within the environment of the missing defective pixel 12.2 (e.g., following the correction step). An interpolation is carried out as a weighted summation across neighboring pixels 12, where the individual weighting factors are yielded from the inverse of the distance. However, if a missing virtual pixel 12.1 lies between two detector modules 24, the missing virtual pixel 12.1 has at least two peripheral pixels 12 with poor signal quality as direct neighbors. This is suppressed within the scope of the interpolation by inclusion of the signal contents of the peripheral pixels 12 in the summation with a very small weighting factor in comparison with more distant pixels 12 considered. In a fourth act S8.4, use is made of both the corrected raw image data and the calculated further raw image data in order to calculate a result X-ray image. Further image processing or image post-processing, such as, for example, a noise treatment of the X-ray image or also a conversion of grayscale information into color information, may be included therein.

The sequence of the acts is to be understood in this context as by way of example only and may be more beneficial in a different order according to other embodiments of the method. In this regard, the exemplary embodiment is to be understood as non-limiting.

Figure 9:
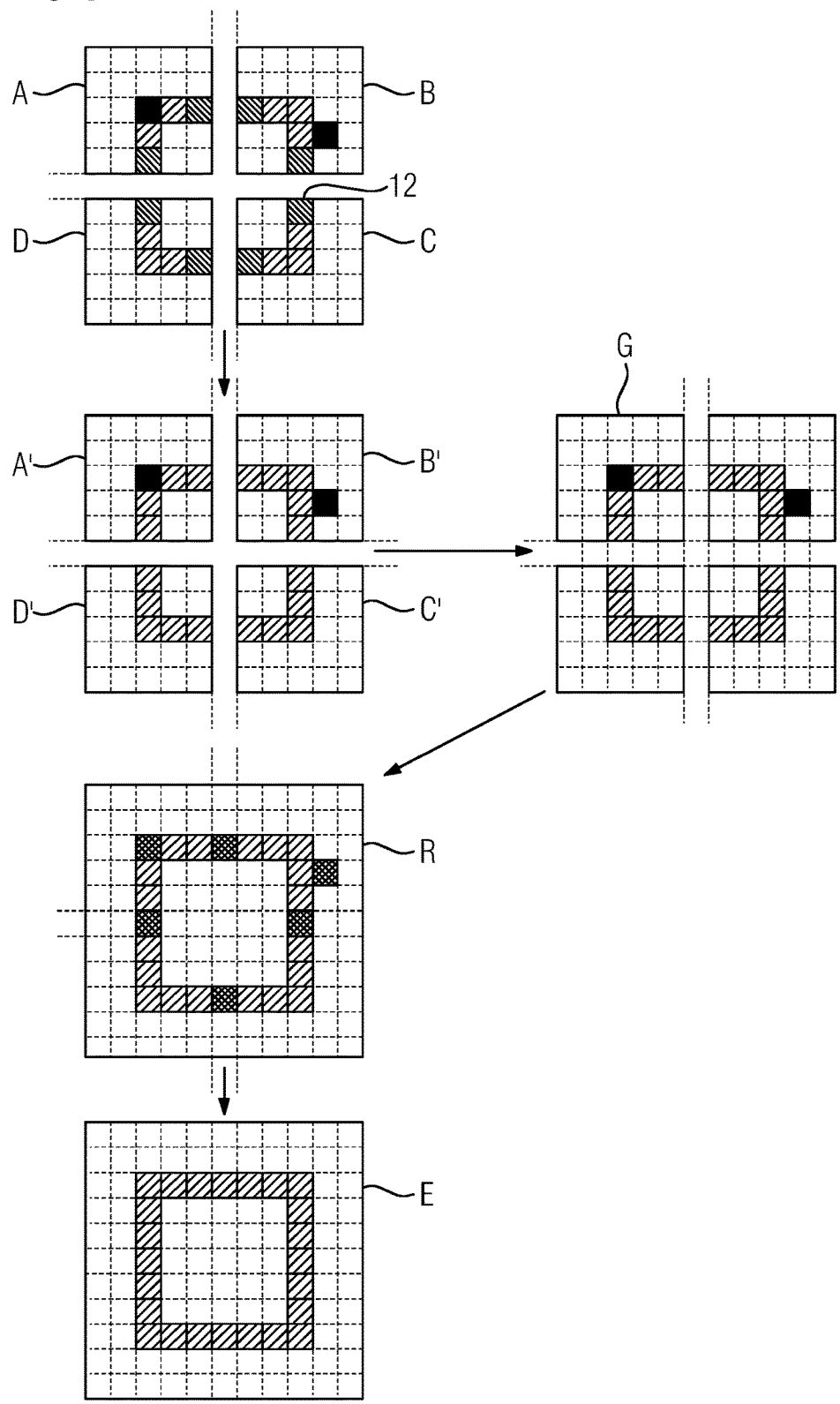
FIG. 9 shows exemplary image data associated with the detector modules depicted in FIG. 7 according to different processing acts of one embodiment of the method.

The acquired raw image data may be present in the form of raw partial images, where each raw partial image represents the image contents acquired by one detector module 24. FIG. 9 illustrates by way of example the raw partial images A, B, C and D of the four detector modules 24 shown in FIG. 7. The raw partial images A and B contain no image information (e.g., black area) at the positions of the defective pixels 12.2 shown in FIG. 7. The signal response of edge pixels of the detector module 24 is systematically different from the signal response of the remaining pixels due to the field inhomogeneities prevailing there. The acquired image information is markedly different (e.g., changed hatching of the depicted structure at the edge). The corrected raw partial images A', B', C' and D' shown in FIG. 9 have passed through a correction act and experienced an alignment of their pixel-specific signal responses during the correction. In other words, the signal contents of the individual pixels have been adjusted to a uniform signal response. This is expressed by way of example by a uniform (e.g., statistical fluctuations aside) signal response also in the edge pixels (e.g., aligned hatching in the depicted structure). The defective pixels 12.2 were excluded from consideration during the correction. The corrected raw partial images A', B', C' and D' may be combined by a stitching algorithm to form a raw total image G, which also provides pixels corresponding to the virtual pixels 12.1 shown in FIG. 7 between the detector modules 24. Stitching algorithms of the type are known from a wide range of application areas (e.g., in multi-CCD detectors for radiography/mammography or in satellite images or constellation images that, when combined, produce a greater view). Such an algorithm is described, for example, in the publication U.S. Pat. No. 6,718,011 B2. As a result of the calculation (e.g., the interpolation) of further image information for the virtual pixels 12.1 between the detector modules 24 as well as the missing defective pixels 12.2 within the detector modules 24, a raw X-ray image R that completely fills the image surface area corresponding to the sensor surface formed by the four detector modules 24 with image information is produced. In spite of or precisely because of the performed correction and/or calculation, the corrected and the supplemented raw image data may have noise components that differ significantly from one another. These are aligned by known noise correction methods in order to generate the result X-ray image E. In the result X-ray image E, the former pixel boundaries are no longer recognizable owing to a homogeneous noise impression.

FIG. 10 shows a flowchart of a method according to a further exemplary embodiment. FIG. 10 shows the individual acts leading from the readout of the individual detector modules 24 to a finished result X-ray image.

The image data acquisition is preceded by a calibration of the X-ray detector 17 in act S10.0. The act may be carried out at any time prior to an acquisition of image data. In the calibration, the conditions for the image acquisition are taken into account (e.g., the X-ray spectrum of the incident X-ray radiation, particular features of the examination subject, the temperature of the room, etc). Different calibration data may exist or be obtained by interpolation of existing calibration data for different acquisition conditions (e.g., different spectra of incident X-ray radiation). Calibration data CalDat including the following correction data or correction functions may be derived within the scope of the calibration.

A position-dependent gain map $G=G(x,y)$ or $G=G(x, y, kVp, f, T, \ldots)$ serves to align the signal response of pixels within a module or the sensor surface of an X-ray detector 17, where f=X-ray flux and T=temperature. Given uniform irradiation of a detector module 24, the same count rate is to be expected (except for statistical fluctuations) in the pixels 12. In reality, a different (e.g., a lower) count rate is measured during the calibration (e.g., in the case of the peripheral pixels, due to the different characteristics of the electrical field for collecting the charge carriers at the edge of the module 24, but also due to other physical effects, such as k-escape, Compton scattering, or simply a smaller effective detector surface area of the edge pixels). The discrepancy between the measured count rate in peripheral and centrally located pixels 12 may be used in order to compensate for the "false" count rate of the peripheral pixels. For example, the deviation in the count rate determined during the calibration is translated into a correction factor for each pixel that is applied to each count content in the course of the correction. The correction factors associated with all pixels relating to an image acquisition configuration together produce a gain map as a result. A position-dependent defect map $D=D(x,y)$ or $D=D(x, y, \ldots)$ indicates where real, defective pixels are present within the sensor surface of an X-ray detector 17. A location-dependent weighting function $W=W(x,y)$ or $W=W(x,y,kVp)$ assigns a weighting factor, where necessary taking into account the X-ray tube voltage, to the surrounding pixels 12 for each missing pixel at the position x,y within the sensor surface. A module correction function $M=Mij$ includes, for each module 24 within a module matrix of an X-ray detector 17, correction values for compensating for module-specific behavior that may be different, for example, due to a variation in the global energy thresholds from module to module or differences in the converter material, which is embodied, not covering a large surface area, but in smaller tiles (e.g., one tile per ASIC). A noise map $R(x,y)$ provides, based on the actually prevailing local noise performance, pixel-by-pixel correction values for achieving a homogenization of the noise.

In act S10.1, the signal contents of individual detector modules 24 are read out pixel-by-pixel (e.g., row-by-row) and form raw image data. In act S10.2, the raw image data is subjected to a module-specific correction. The signal contents of all pixels of a module 24 are adjusted to achieve a uniform signal response. Module-specific calibration data CalDat in the form of a gain map $G(x,y)$ is used for this purpose. For counting energy-discriminating detectors, a correction is performed individually for each energy threshold or each energy bin. Accordingly, the calibration data CalDat is present for individual threshold values or energy bins or may be derived from existing data. The corrected raw image data is then modified in act S10.3 in that signal contents are calculated for missing pixels (e.g., virtual and/or defective real pixels). In the case of missing rows or columns of pixels between detector modules 24, the missing image content is interpolated. The image contents of neighboring pixels from the environment of a missing pixel are added together on a weighted basis, with nearest neighbors of the missing pixel in the form of peripheral pixels of the adjacent detector modules being taken into account with a small weighting factor or the smallest of all of the weighting factors. The next-nearest neighbors of the missing pixel as well as the neighbors lying in the third and fourth row are included in the weighting with a heavily weighted factor or with the largest weighting factors. Compared to the peripheral pixels, the pixels exhibit a good signal quality and are arranged sufficiently closely to the missing pixel to achieve a good spatial resolution. If more distant pixel rows are also taken into account in the interpolation, these contribute only to a subordinate extent to the summation as a function of the inverse of their distance.

FIG. 11 shows, by way of example, a possible weighting function W(x,y) employed in this connection. The weighting function W(x,y) serves for restoring virtual missing virtual pixels 12.1 between detector modules based on the signal and noise quality of the pixels 12 surrounding the virtual pixels 12.1. The lines used for the illustration are intended simply to indicate the characteristic curve of the weighting function W(x,y) over an X-ray detector 17 composed of four square-shaped and adjacently arranged detector modules 24 (similar to FIG. 7) and do not reflect the location of the individual pixels 12. Pixels 12 directly next to the virtual pixels 12.1 between the detector modules 24 and pixels 12 at a distance of more than three or four pixels 12 are barely included in the summation. In the case of missing pixels at the outer edge of a detector module 24 arranged peripherally in the sensor surface, the missing image content is extrapolated in an analogous manner due to the absence of an adjacent detector module 24. If a missing pixel 12 is a defective real pixel 12.2 that is a direct neighbor to a peripheral pixel 12 of a detector module 24 or is adjacent in the second, third or fourth row, this is taken into account in the calculation of the new image content for the missing pixel. Accordingly, the interpolation is performed in this case as a weighted summation over the signal contents of the neighboring pixels using weighting factors that behave substantially inversely to the distance of the pixels under consideration in order to ensure a good spatial resolution. Only the weighting factor of the peripheral pixel or pixels is disproportionately small and consequently no longer inverse to the distance in order to suppress the image errors included in the signal content. In the calculation of missing or new image information for missing defective pixels 12.2 within a detector module 24 at a sufficiently great distance from the edge, the interpolation is performed as a weighted summation of the signal contents of all pixel neighbors having weighting factors that behave substantially inversely to the distance of the considered pixels in order to provide a best possible spatial resolution. Up to which degree of neighbor proximity the surrounding pixels are taken into account is firstly application-specific, is dependent on the geometry of the X-ray detector 17, and is also determined by the actual choice of the weighting function W(x,y). For example, for the square-shaped pixel geometry, direct neighbors may be the pixels that have a center point spaced at the distance of a pixel pitch 53a and/or according to a pixel diagonal pitch 53b from the center point of a missing pixel; neighbors in the second row accordingly have a distance corresponding to the double of the pixel pitch 53a or of the pixel diagonal pitch 53b, etc. However, this assignment is arbitrary and, for example, also geometry-dependent. For counting energy-discriminating X-ray detectors, the calculation acts just described are performed separately for all energy threshold values or energy bins. In order to create a homogeneously appearing noise impression throughout the X-ray image that is to be generated, noise reduction or noise algorithms known per se are applied in a subsequent act S10.4 to the local image processing at the edges and across the module boundaries. Due to the reduced quantum statistics, the frequently lower count rates of the peripheral pixels consequently also generate a higher relative noise. After the count rates have been adjusted as a result of the correction, the noise in the peripheral pixels is higher than in more centrally located pixels. However, the increased noise is also deterministically predictable by the calibration process and may be compensated by suitable noise reduction measures (e.g., by the noise map R(x,y)), which are likewise based on the calibration data CalDat. In other words, the noise signal of the signal contents of peripheral pixels, which was likewise enhanced as well as a result of the alignment of the signal response in act S10.2, is reduced, and the noise signal of the interpolated or extrapolated signal contents of missing pixels between modules or at the edge of the sensor surface is enhanced based on the calibration data CalDat, which overall results in a noise alignment. This causes the detector module boundaries to be made unrecognizable in the result X-ray image. In the case of counting energy-selective pixels, the noise adjustment is obviously carried out separately for each energy threshold or each bin. In act S10.5, further corrections or alignments may be carried out if desired or necessary (e.g., an alignment of the module-specific response behavior by the module correction function Mij, provided these have not (e.g., not yet) been corrected within the scope of act S10.2. For this purpose, too, recourse may be made to the detector-specific calibration data CalDat. An X-ray image that represents image contents irrespective of the position in the image (e.g., has no regions with missing or unrealistic image information, having a substantially homogeneous spatial resolution and homogeneous noise signal) is produced.

The sequence of the acts is to be understood in this context as exemplary only and may be more beneficial in a different order according to other variants of the method. In this regard, the exemplary embodiment is to be understood as non-limiting.

Additional acts not mentioned explicitly may likewise be performed within the scope of one or more of the present embodiments. For example, the acquisition of the raw image data may be preceded by a pixel-by-pixel adjustment of the discriminator thresholds in order to provide that the counting process is performed for each pixel above the same energy threshold or within the same energy bins. This brings about a better comparability of the acquired raw image data. The adjustment may be carried out within a module, on a cross-module basis, and/or, in the case of energy-selective detectors, for each individual energy threshold or each bin.

FIG. 12 shows an X-ray system 16 having a data processing device 20 in an exemplary embodiment. The X-ray system 16 includes an X-ray tube 18 and an X-ray detector 17, arranged jointly on a C-arm 19, for example, and a high-voltage generator for generating the tube voltage (not shown). The X-ray detector 17 is formed by a flat-panel image detector. Such a flat-panel image detector may be utilized, for example, in X-ray systems for interventional procedures (e.g., in cardiology, radiology, and in surgery or in the monitoring of a radiotherapy planning protocol or mammography). In addition to the application as a flat-panel image detector, an X-ray detector 17 may also be used as a curved linear detector (e.g., in computed tomography). The X-ray detector 17 may be embodied as a digital counting X-ray detector (e.g., as a counting energy-discriminating X-ray detector). The X-ray system 16 further includes a data processing device 20, a system control unit 21 typically included therein, and a patient table 23. Biplane systems (e.g., two C-arms) are likewise employed in interventional radiology. The data processing device 20 in the form of a computer includes a display unit 22, for example, to allow the graphical display of reconstructed X-ray images (e.g., result images) or for displaying a user interface for a user. The display unit 22 may be an LCD, plasma or OLED screen. The display unit 22 may also be a touch-sensitive screen. The system control unit 21 is configured for generating control commands for the X-ray system 16 and transferring the same to the X-ray system 16. For this purpose, the data processing device 20 is connected to the X-ray tube 18 and/or the C-arm 19. The data processing device 20 is also connected to the X-ray detector 17 for data exchange purposes. To this end, the data processing device 20 includes an interface unit 204 that is embodied for acquiring X-ray raw image data from a plurality of detector modules 24 of the X-ray detector 17 for further processing by the data processing device 20. The data processing device 20 further includes a correction unit 203 configured for at least partially correcting the acquired raw image data. The correction includes, for example, an alignment of the signal responses of the individual pixels 12 within a detector module 24. The correction unit 203 is connected to a memory unit 205 that is included in the data processing device 20 and in which correction data for the individual pixels is stored in retrievable form in each case for different acquisition parameters. In the event that no matching correction data is present for the current image data acquisition, the correction unit 203 is configured to calculate the desired correction data from the available correction data, by an interpolation, for example. The data processing device 20 further includes a first calculation unit 202 that is configured to calculate further raw image data for at least one missing pixel 12.1, 12.2 using the corrected raw image data. The computational operations are interpolation or extrapolation operations. In this case, a weighted summation is performed for each missing pixel across neighboring pixels. A selection of different weighting factors is stored in a memory unit 205 ready for retrieval by the first calculation unit 202. The data processing device 20 also includes a further calculation unit 201 configured to calculate an X-ray image based on the corrected and the further raw image data. To allow the corrected raw image data and the further raw image data to be accessed, the further calculation unit 201 is connected via a data link to the correction unit 203 and to the first calculation unit 202, respectively. The further calculation unit 201 generates an X-ray image from the raw image data by assigning a position in an image matrix to the pixel-by-pixel image information according to the sensor surface of the X-ray detector 17 and thereby linking the image contents to one another. The further calculation unit 201 is additionally configured to apply further corrections (e.g., a noise algorithm) to the X-ray image. The further calculation unit 201 may include a noise correction unit 201.a that is connected to the memory unit 205 to allow the retrieval of further calibration data required for that purpose. The finished X-ray image may be transferred for visualization purposes from the further calculation unit 201 to the display unit 22. Correction unit 203, first calculation unit 202, and further calculation unit 201 may alternatively form one unit. The described connections between the units of the X-ray system 16 may be implemented in a known manner in hardwired or wireless form.

The data processing device 20 may cooperatively interact with a computer-readable data medium (e.g., in order to perform a method according to the present embodiments by a computer program containing program code). The computer program may be stored on the machine-readable medium in retrievable form. For example, the machine-readable medium may be a CD, DVD, a Blu-ray Disc, a memory stick, or a hard disk. The data processing device 20 may be embodied in the form of hardware or in the form of software. For example, the data processing device 20 is embodied as a device known as a Field Programmable Gate Array (FPGA) or includes an arithmetic logic unit.

In the example shown here, there is stored in the memory 205 of the data processing device 20 at least one computer program that performs all of the method acts of the method according to the present embodiments when the computer program is executed on the computer. The computer program for performing the method acts of the method according to one or more of the present embodiments includes program code. The computer program may be embodied as an executable file and/or be stored on a different computing system from the data processing device 20. For example, the X-ray system 16 may be configured such that the data processing device 20 loads the computer program for performing the method according to one or more of the present embodiments into an internal random access memory via an intranet or via the Internet.

The memory 205 of the data processing device 20 is embodied for storing calibration data CalDat for a plurality of X-ray image acquisition conditions. Alternatively, the data processing device 20 is connected to a Radiological Information System (RIS) network in order to retrieve the cited information, which in this case may be stored in the RIS network.

Figure 13:
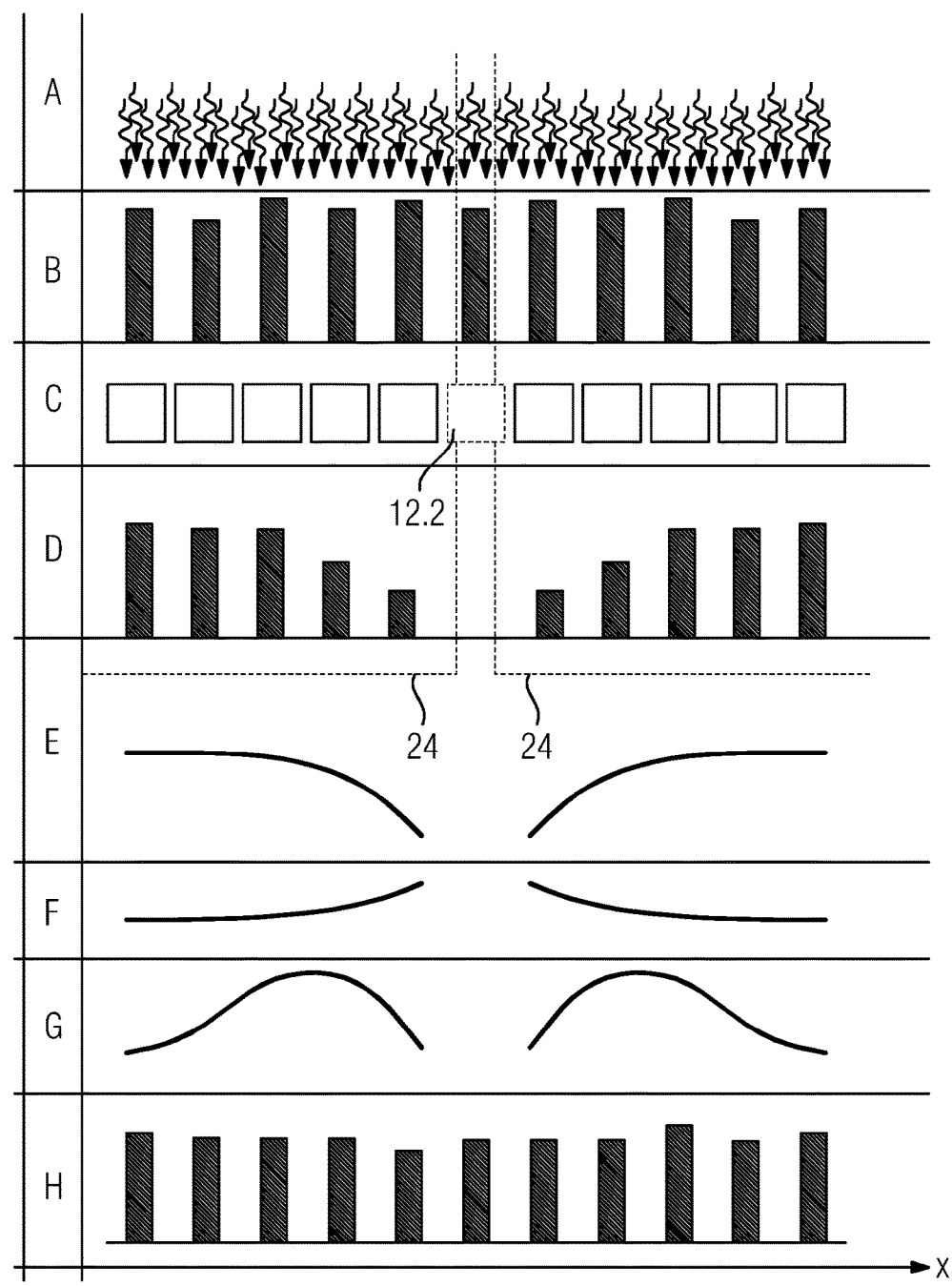
FIG. 13 shows an overview that illustrates an exemplary embodiment.

The present embodiments are briefly summarized with reference to FIG. 13. The horizontal axis x extends through a pixel row of an X-ray detector 17 according to row C including two detector modules 24 with a missing pixel 12.1 lying therebetween. Row A shows the X-ray photon flux that is incident on the pixel row. Disregarding the Poisson statistics, this may be distributed homogeneously over the pixel row. This is expressed in a number of photons incident per pixel that varies slightly across the pixel row according to row B. A part of the incident X-ray quanta is absorbed in the corresponding pixels, another part is only scattered or passes through the examination subject without interaction. Row D illustrates the number of photons measured per pixel, which deviates significantly from the number of incident photons, for example, at the module boundaries, in practice is reduced compared thereto. Because of the differing response function at the module edges, the signal response (shown in row E) as well as the relative noise ratio (shown in row F) varies in the peripheral pixels across the pixel row. In order to align the signal response, one or more of the present embodiments make provision for performing an enhancement (e.g., a percentage enhancement) of the count signals of the peripheral pixels (not shown). In order to supplement image information in the missing pixel 12.1 within the pixel row, one or more of the present embodiments provide a weighting function $W(x)$ (e.g., a one-dimensional weighting function), which is shown in row G. This weights the signal contents of the next-nearest neighbors and neighbors in the third row particularly heavily, whereas the peripheral pixels and more distant pixels are barely or only weakly included in the weighting. In the overall context of the corrected count signals of the peripheral pixels as well as the interpolated count signal of the missing pixel, a continuous X-ray image without vacancies is produced as a result.

Although the invention has been illustrated in more detail on the basis of the exemplary embodiments, the invention is not limited by the disclosed examples. Other variations can be derived herefrom by the person skilled in the art without leaving the scope of protection of the invention. For example, features of the described exemplary embodiments can be interchanged where this is technically possible and beneficial.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for generating an X-ray image of an object using an X-ray system, the X-ray system comprising a counting X-ray detector, the counting X-ray detector comprising a common substrate and a plurality of detector modules that are alignable adjacent to one another, wherein each detector module of the plurality of detector modules comprises an X-ray converter and is subdivided into a matrix having a plurality of pixels, wherein the plurality of detector modules are arranged adjacent to one another on the common substrate, wherein a sensor surface formed by the plurality of detector modules has a uniform matrix structure having a constant pixel pitch, wherein at least one missing pixel is arranged within the sensor surface, the method comprising:

acquiring raw image data from the plurality of detector modules of the counting X-ray detector;

at least partially correcting the acquired raw image data;

calculating further raw image data for the at least one missing pixel using the at least partially corrected acquired raw image data; and calculating the X-ray image based on the at least partially corrected acquired raw image data and the calculated further raw image data.

2. The method of claim 1, wherein at least partially correcting the acquired raw image data comprises adjusting signal contents of a portion of the plurality of pixels with regard to a uniform signal response at least within a corresponding detector module.

3. The method of claim 2, wherein at least partially correcting the acquired raw image data comprises taking into account a spectrum of X-ray radiation applied in order to acquire the raw image data.

4. The method of claim 2, wherein at least partially correcting the acquired raw image data comprises multiplying the signal contents of the portion of the plurality of pixels by a previously determined correction factor.

5. The method of claim 2, wherein at least partially correcting the acquired raw image data comprises suppressing noise with respect to the signal contents of the portion of the plurality of pixels.

6. The method of claim 2, wherein calculating the further raw image data comprises interpolating, extrapolating, or interpolating and extrapolating the at least partially corrected acquired raw image data onto the at least one missing pixel.

7. The method of claim 6, wherein the interpolating, the extrapolating, or the interpolating and the extrapolating comprise weighted summing of the signal contents of the plurality of pixels surrounding the at least one missing pixel.

8. The method of claim 7, further comprising weighting the signal contents of the plurality of pixels surrounding the at least one missing pixel as a function of a distance between an individual pixel of the plurality of pixels and a missing pixel of the at least one missing pixel.

9. The method of claim 7, further comprising incorporating pixels of the plurality of pixels arranged peripherally on a detector module of the plurality of detector modules with a weakest weighting when the at least one missing pixel is arranged between two detector modules of the plurality of detector modules and has peripheral pixels of the plurality of pixels of at least one detector module of the plurality of detector modules, has further missing pixels of the at least one missing pixel as direct neighbors, or has a combination thereof, is arranged close to an edge of the detector module and has peripheral pixels of the plurality of pixels of the detector module as direct neighbors, or a combination thereof.

10. The method of claim 7, further comprising incorporating pixels of the plurality of pixels that are spaced at a distance from the at least one missing pixel corresponding to a double, triple, or quadruple of the constant pixel pitch with a heaviest weighting when the at least one missing pixel is arranged between two detector modules of the plurality of detector modules and has peripheral pixels of the plurality of pixels of at least one detector module of the plurality of detector modules, has further missing pixels of the at least one missing pixel as direct neighbors, or has a combination thereof.

11. The method of claim 6, further comprising noise enhancing with respect to the calculated further raw image data for the at least one missing pixel.

12. The method of claim 2, wherein the portion of the plurality of pixels comprises pixels arranged in edge zones of a detector module of the plurality of detector modules.

13. The method of claim 1, further comprising adjusting a discriminator threshold value corresponding to a desired X-ray quantum energy to be detected in a pixel-specific manner prior to the acquiring of the raw image data.

14. The method of claim 1, wherein the at least one missing pixel is arranged between neighboring detector modules of the plurality of detector modules, at an outer edge of detector modules of the plurality of detector modules arranged peripherally in the sensor surface, or between the neighboring detector modules of the plurality of detector modules and at the outer edge of the detector modules of the plurality of detector modules arranged peripherally.

15. A data processing device of a counting X-ray detector, of an X-ray system comprising the counting X-ray detector, or of the counting X-ray detector and the X-ray system, the X-ray system comprising a common substrate and a plurality of detector modules that are alignable adjacent to one another, wherein each detector module of the plurality of detector modules comprises an X-ray converter and is subdivided into a matrix having a plurality of pixels, wherein the plurality of detector modules are arranged adjacent to one another on the common substrate, wherein a sensor surface formed by the plurality of the detector modules has a uniform matrix structure having a constant pixel pitch, wherein at least one missing pixel is arranged within the sensor surface, the data processing device comprising:

a processor configured to:

acquire raw image data from the plurality of detector modules of the counting X-ray detector;

at least partially correct the acquired raw image data;

calculate further raw image data for the at least one missing pixel using the at least partially corrected acquired raw image data; and calculate an X-ray image based on the at least partially corrected acquired raw image data and the calculated further raw image data.

16. The data processing device of claim 15, wherein the processor is further configured to adjust signal contents of a portion of the plurality of pixels with regard to a uniform signal response at least within a detector module of the plurality of detector modules.

17. The data processing device of claim 16, wherein the data processing device further comprises a correction unit, and wherein the correction unit is configured to adjust signal contents of pixels of the plurality of pixels arranged in edge zones of a detector module of the plurality of detector modules.

18. The data processing device of claim 15, wherein the processor is configured to calculate the further raw image data for the at least one missing pixel using an interpolation, extrapolation, or interpolation and extrapolation of the at least partially corrected raw image data onto the at least one missing pixel.

19. The data processing device of claim 15, further comprising a noise correction unit configured to apply noise reduction or noise enhancement algorithms to the at least partially corrected acquired raw image data, the calculated further raw image data, or the at least partially corrected acquired raw image data and the calculated further raw image data.

20. The data processing device of claim 15, wherein the at least one missing pixel is arranged between neighboring detector modules of the plurality of detector modules, at an outer edge of detector modules of the plurality of detector modules arranged peripherally in the sensor surface, or between the neighboring detector modules and at the outer edge of the detector modules of the plurality of detector modules arranged peripherally in the sensor surface.

* * * * *